United States Patent
Yamamoto et al.

(10) Patent No.: US 9,180,207 B2
(45) Date of Patent: Nov. 10, 2015

(54) EPO KNOCKOUT GFP ANEMIC MOUSE

(75) Inventors: Masayuki Yamamoto, Miyagi (JP); Naoko Minegishi, Miyagi (JP); Shun Yamazaki, Miyagi (JP)

(73) Assignee: TOHOKU TECHNO ARCH CO., LTD., Miyagi (JP)

(*) Notice: Subject to any disclaimer, the term of this patent is extended or adjusted under 35 U.S.C. 154(b) by 0 days.

(21) Appl. No.: 14/008,703

(22) PCT Filed: Mar. 29, 2012

(86) PCT No.: PCT/JP2012/002207
§ 371 (c)(1),
(2), (4) Date: Sep. 30, 2013

(87) PCT Pub. No.: WO2012/137449
PCT Pub. Date: Oct. 11, 2012

(65) Prior Publication Data
US 2014/0053288 A1    Feb. 20, 2014

(30) Foreign Application Priority Data
Apr. 5, 2011 (JP) .................... 2011-083664

(51) Int. Cl.
*A01K 67/027* (2006.01)
*A01K 67/033* (2006.01)
*A61K 49/00* (2006.01)
*G01N 33/50* (2006.01)

(52) U.S. Cl.
CPC ......... *A61K 49/0008* (2013.01); *A01K 67/0276* (2013.01); *A01K 67/0278* (2013.01); *G01N 33/502* (2013.01); *A01K 2217/075* (2013.01); *A01K 2227/105* (2013.01); *A01K 2267/01* (2013.01); *A01K 2267/0381* (2013.01); *G01N 2333/505* (2013.01)

(58) Field of Classification Search
None
See application file for complete search history.

(56) References Cited

PUBLICATIONS

Clark et al. 2003, Nature Reviews 4: 825-833.*
International Search Report for Application No. PCT/JP2012/002207 dated Jun. 19, 2012.
Zeigler B.M. et al., A mouse model for an erythropoietin-deficiency anemia, Dis.Model. Mech., 2010, vol. 3, pp. 763-772.
Maxwell P.N. et al., Identification of the renal erythropoietin-producing cells using transgenic mice, Kidney Int., 1993, vol. 44, pp. 1149-1162.
Shun Yamazaki et al., Rescue of Erythropoietin null mice and conditional inactivation of Erythropoietin, Journal of Japanese Biochemical Society, Shoroku CD, 2009, p. Rombunno. 4T4p-11 together with the English translation thereof.
Shun Yamazaki et al., Influence of Conditional Inactivation of Erythropoietin Gene on Adult Erythropoiesis, Journal of Japanese Biochemical Society, Shoroku CD, 2010, p. Rombunno. 1P-0304 together with English translation thereof.
Obara N. et al., Repression via the GATA box is essential for tissue-specific erythropoietin gene expression, Blood, 2008, vol. 111, pp. 5223-5232.
Pan X. et al., Isolation and characterization of renal erythropoietin-producing cells from genetically produced anemia mice, PLoS One, Oct. 2011, vol. 6, e25839, pp. 1-11.
Takeda A. et al., Factors Contributing to Higher Hematocrit Levels in Hemodialysis Patients not Receiving Recombinant Human Erythropoietin. American Journal of Kidney Diseases, 2002; vol. 40, pp. 104-109.
Gagnon RF and Duguid WP., A reproducible model for chronic renal failure in the mouse. Urological Research. 1983; vol. 11, pp. 11-14.
Gagnon RF and Gallimore B., Characterization of a mouse model of chronic uremia. Urological Research. 1988; vol. 16, pp. 119-126.
Garcia DL et al., Anemia lessens and its prevention with recombinant human erythropoietin worsens glomerular injury and hypertension in rats with reduced renal mass. Proceedings of the National Academy of Sciences of the United States of America. 1988; vol. 85, pp. 6142-6146.
Wu H. et al., Generation of committed erythroid BFU-E and CFU-E progenitors does not require erythropoietin or the erythropoietin receptor. Cell. 1995; vol. 83, pp. 59-67.
Yamazaki, S. et al., Rescue of Erythropoietin-Deficient Mice from Anemia by Complementation with BAC Transgene. Blood (ASH Annual Meeting Abstracts), Nov. 2009; vol. 114, pp. 3614.
Zeigler Bm et al., A mouse model for an erythropoietin-deficiency anemia. Disease Models & Mechanisms. 2010, vol. 3, pp. 763-772.
Kapitsinou PP et al. Hepatic HIF-2 regulates erythropoietic responses to hypoxia in renal anemia. Blood. 2010; vol. 116, pp. 3039-3048.
Maxwell PH et al. Identification of the renal erythropoietin-producing cells using transgenic mice. Kidney International. 1993; vol. 44, pp. 1149-1162.
Raja El Hasnaoui-Saadani et al. Cerebral adaptations to chronic anemia in a model of erythropoietin-deficient mice exposed to hypoxia. American Journal of Physiology—Regulatory Integrative & Comparative Physiology. 2009; vol. 296, pp. R801-R811.
Rinsch C et al. Delivery of erythropoietin by encapsulated myoblasts in a genetic model of severe anemia. Kidney International. 2002; vol. 62, pp. 1395-1401.
Binley K et al. Long-term reversal of chronic anemia using a hypoxia-regulated erythropoietin gene therapy. Blood. 2002; vol. 100, pp. 2406-2413.
Gruber M et al. Acute postnatal ablation of Hif-2 {alpha} results in anemia. Proceedings of the National Academy of Sciences USA. 2007; vol. 104, pp. 2301-2306.
Suzuki N et al. Use of Gene-Manipulated Mice in the Study of Erythropoietin Gene Expression. Methods in Enzymology. Academic Press, 2007, vol. 435, pp. 157-177.
Obara N et al. Repression via the Gata box is essential for tissue-specific erythropoietin gene expression. Blood. 2008; vol. 111, pp. 5223-5232.
Extended European Search Report, European Appl. No. 12768270.6-1405, PCT/JP2012002207, mailed Nov. 18, 2014, pp. 1-12.

(Continued)

Primary Examiner — Doug Schultz
(74) Attorney, Agent, or Firm — Pearne & Gordon LLP

(57) ABSTRACT

The present invention relates to a model animal spontaneously developing anemia. More specifically, the invention relates to a transgenic non-human mammal spontaneously developing anemia associated with a postnatal decrease in production of erythropoietin (Epo), Epo-producing cells prepared from the transgenic non-human mammal, and a screening method using the Epo-producing cells.

3 Claims, 21 Drawing Sheets

(56) References Cited

PUBLICATIONS

Mukai, H. Y. et al.: "Transgene Insertion in Proximity to the c-myb Gene Disrupts Erythroid-Megakaryocytic Lineage Bifurcation", Molecular and Cellular Biology, vol. 26, No. 21, Aug. 28, 2006, pp. 7953-7965.

Kochling, J. et al.: "Regulation of human erythropoietin gene induction by upstream flanking sequences in transgenic mice", British Journal of Haematology, vol. 103, 1998, pp. 960-968.

Haidar, M. A. et al.: "Differential expression of lacZ in the liver and kidney of transgenic mice carrying chimeric lacZ-erythropoietin gene constructs with or without its 1.2 kb 3'-flanking sequence", Nucleic Acids Research, vol. 24, No. 18, 1996, pp. 3621-3628.

Madan, A. et al.,: "Regulated Basal, Inducible, and Tissue-Specific Human Erythropoietin Gene Expression in Transgenic Mice Requires Multiple cis DNA Sequences", Blood, vol. 85, No. 10, 1995, pp. 2735-2741.

Semenza, G. L. et al.: "Cell-type-specific and hypoxia-inducible expression of the human erythropoietin gene in transgenic mice", Proc. Natl. Acad. Sci. USA, vol. 88, Oct. 1991, pp. 8725-8729.

Semenza, G. L. et al.: "Hypoxia-inducible nuclear factors bind to an enhancer element located 3' to the human erythropoietin gene", Proc. Natl. Acad. Sci. USA, vol. 88, Jul. 1991, pp. 5680-5684.

Suzuki, N. et al.: "Specific Contribution of the Erythropoietin Gene 3' Enhancer to Hepatic Erythropoiesis after Late Embryonic Stages", Molecular and Cellular Biology, vol. 31, No. 18, Sep. 2011, pp. 3896-3905.

Yamazaki, S. et al.,: "A mouse model of adult-onset anaemia due to erythropoietin deficiency", Nature Communications, vol. 4, 3 Jun. 2013, pp. 1-12.

Querbes, W. et al.,: "Treatment of erythropoietin deficiency in mice with systemically administered siRNA", Blood, vol. 120, No. 9, Aug. 30, 2012, pp. 1916-1922.

\* cited by examiner

FIG.5

| Crossing | | Pups | Epo +/+ | | Epo +/- | | Epo -/- | |
|---|---|---|---|---|---|---|---|---|
| | | | Tg (-) | Tg (+) | Tg (-) | Tg (+) | Tg (-) | Tg (+) |
| Epo +/- ; 3.3K-Epo3' × Epo +/- | line444 | 53 | 6 (11%) | 5 (9%) | 21 (40%) | 21 (40%) | 0 (0%) | 0 (0%) |
| | line458 | 20 | 2 (10%) | 1 (5%) | 4 (20%) | 7 (35%) | 0 (0%) | 6 (30%) |
| | line475 | 28 | 3 (11%) | 5 (18%) | 10 (36%) | 7 (25%) | 0 (0%) | 3 (11%) |
| | line476 | 26 | 7 (27%) | 4 (15%) | 7 (27%) | 5 (19%) | 0 (0%) | 3 (12%) |
| | Expected | | 14% | 14% | 29% | 29% | 0% | 14% |
| Epo -/- ; 3.3K-Epo3' × Epo +/- | line458 | 66 | — | — | 32 (49%) | 18 (27%) | 0 (0%) | 16 (24%) |
| | line475 | 26 | — | — | 9 (35%) | 9 (35%) | 0 (0%) | 8 (31%) |
| | line476 | 10 | — | — | 2 (20%) | 5 (50%) | 0 (0%) | 3 (30%) |
| | Expected | | | | 33% | 33% | 0% | 33% |
| Epo -/- ; 3.3K-Epo3' × Epo -/- ; 3.3K-Epo3' | line458 | 11 | — | — | — | — | 0 (0%) | 11 (100%) |
| | line475 | 10 | — | — | — | — | 0 (0%) | 10 (100%) |
| | Expected | | | | | | 0% | 100% |

FIG.14

A (8 to 10 WEEKS OF AGE)

| Genotype | | WBC (x100/uL) | RBC (x10⁶/μL) | HGB (g/dL) | HCT (%) | MCV (fL) | MCH (pg) | MCHC (g/dL) | PLT (x10⁴/uL) | Body weight (g) |
|---|---|---|---|---|---|---|---|---|---|---|
| I-Sam n=14 | Mean | 46.9 | 2.9 | 4.7 | 14.2 | 49.9 | 16.5 | 33.1 | 93.9 | 24.2 |
|  | SD | 17.8 | 0.6 | 1.0 | 3.0 | 0.8 | 0.5 | 0.8 | 16.1 | 2.9 |
| Control n=4 | Mean | 88.8 | 9.2 | 15.1 | 44.2 | 48.0 | 16.4 | 34.1 | 83.6 | 23.4 |
|  | SD | 31.4 | 0.4 | 0.6 | 2.3 | 1.4 | 0.2 | 0.6 | 17.9 | 1.1 |

B (1 YEAR OF AGE)

| Genotype | | WBC (x100/uL) | RBC (x10⁶/μL) | HGB (g/dL) | HCT (%) | MCV (fL) | MCH (pg) | MCHC (g/dL) | PLT (x10⁴/uL) | Body weight (g) |
|---|---|---|---|---|---|---|---|---|---|---|
| I-Sam ♂ n=5 | Mean | 43.2 | 2.1 | 3.2 | 10.0 | 46.9 | 15.0 | 32.0 | 80.1 | 38.7 |
|  | SD | 13.3 | 0.3 | 0.5 | 1.3 | 2.5 | 0.9 | 1.4 | 34.2 | 8.2 |
| I-Sam ♀ n=16 | Mean | 53.9 | 3.3 | 5.2 | 15.6 | 47.9 | 15.9 | 33.1 | 113.1 | 40.9 |
|  | SD | 31.5 | 0.4 | 0.5 | 1.6 | 2.0 | 0.7 | 0.9 | 15.2 | 6.9 |
| Control ♀ n=7 | Mean | 53.3 | 8.7 | 13.7 | 41.2 | 47.5 | 15.8 | 33.2 | 89.5 | 41.7 |
|  | SD | 21.1 | 0.8 | 1.0 | 3.3 | 2.0 | 1.0 | 0.7 | 23.5 | 8.1 |

SEQUENCE LISTING

```
<160> NUMBER OF SEQ ID NOS: 5

<210> SEQ ID NO 1
<211> LENGTH: 21
<212> TYPE: DNA
<213> ORGANISM: Artificial
<220> FEATURE:
<223> OTHER INFORMATION: primer(GFP-cs)

<400> SEQUENCE: 1
actctcggca tggacgagct g                                         21

<210> SEQ ID NO 2
<211> LENGTH: 23
<212> TYPE: DNA
<213> ORGANISM: Artificial
<220> FEATURE:
<223> OTHER INFORMATION: primer(Epo-RTR)

<400> SEQUENCE: 2
gtgagtgttc ggagtggagc agg                                       23

<210> SEQ ID NO 3
<211> LENGTH: 21
<212> TYPE: DNA
<213> ORGANISM: Artificial
<220> FEATURE:
<223> OTHER INFORMATION: primer(Epo-5UTRs)

<400> SEQUENCE: 3
acaggaaggt ctcacatagc c                                         21

<210> SEQ ID NO 4
<211> LENGTH: 22
<212> TYPE: DNA
<213> ORGANISM: Artificial
<220> FEATURE:
<223> OTHER INFORMATION: primer(Epo-s5)

<400> SEQUENCE: 4
tacagctagg agagttgtgt gg                                        22

<210> SEQ ID NO 5
<211> LENGTH: 21
<212> TYPE: DNA
<213> ORGANISM: Artificial
<220> FEATURE:
<223> OTHER INFORMATION: primer(Epo-B6as)

<400> SEQUENCE: 5
tggggaaacc cccatgagat c                                         21
```

EPO KNOCKOUT GFP ANEMIC MOUSE

TECHNICAL FIELD

The present invention relates to an animal model spontaneously developing anemia. More specifically, the invention relates to a transgenic non-human mammal spontaneously developing anemia associated with a postnatal decrease in production of erythropoietin (Epo).

BACKGROUND ART

Epo is a cytokine that stimulates erythropoiesis and is also known as a therapeutic agent for renal anemia, having achieved satisfactory treatment for a long time. Epo is mainly produced in the liver (embryonic stage) and the kidney (after birth) of mammals. In chronic renal dysfunction, the Epo production in the kidney decreases to cause anemia (renal anemia) (Non Patent Literature 1). This anemia is cured by administration of Epo prepared by a genetic recombination technology, and thereby the prognosis and the quality of life of renal anemia patients have been dramatically improved.

It has been revealed that Epo in tissues, such as the central nervous system, the retina, the kidney, and the heart, shows cytoprotection against stress, and the clinical use of Epo intended to have an effect other than hematopoiesis has been started in some clinical fields. At the same time, it is also reported, for example, that administration of Epo also stimulates proliferation of cancer cells to cause a decrease in performance of treatment and that administration of Epo facilitates thrombus formation to shorten the lifetime. In the new guidelines of the USA, more strict standards apply to administration of Epo and similar drugs. However, data, such as those of animal experiments, supporting these effects of Epo are insufficient, except for clinical statistical data, and establishment of a useful experimental system has been therefore demanded.

Incidentally, a hypoxia-inducible factor (HIF) has been identified by research on controlling expression of an Epo gene using a hepatocyte-derived cell line, and this factor is now recognized as an important factor in various biological activities such as inflammation, genesis, and carcinogenesis as well as energy metabolism. In the kidney, only a small number of specific cells produce Epo, and it is predicted that an unknown factor regulating tissue specificity and hypoxia reactivity works in the production, and elucidation thereof has high possibility of leading to elucidation of pathological conditions of various diseases and development of a method of treatment. However, the production of Epo is suppressed to be very low under a usual breeding environment. Therefore, Epo-producing cells cannot be identified or analyzed without anemia induction by blood removal or phenylhydrazine administration or stimulation of Epo production, such as breeding in a hypoxia chamber, and such a situation has continued for a long period of time.

Furthermore, there are many reports on control of proliferation and survival of cells by Epo, but research on the differentiation induction mechanism by Epo is few. In the time when Epo was found, it was believed that a receptor of Epo is specifically present in erythroid cells and that Epo mainly functions for supporting the survival of the cells. In the subsequent research, it was believed that Epo may also actively affect the program of erythroid differentiation. However, the detailed mechanism has not been elucidated. Incidentally, erythropoiesis associated with an increase in blood Epo concentration, such as under a high altitude or anemia, is called stress hematopoiesis, and, in mice, the spleen is the place for the hematopoiesis. In general, the Epo concentration in regular hematopoiesis is kept very low. Accordingly, it is predicted that the molecular mechanism of the stress hematopoiesis is different from that of the regular hematopoiesis, but the detail thereof is unclear. Furthermore, in chronic anemia associated with inflammation or cancer, the Epo production and Epo sensitivity decrease, but the mechanism thereof is also unclear.

In order to solve these problems, development of mice with adult-onset deficiency in Epo production has been demanded. Conventionally, in research on renal anemia and acquisition of experimental animals less producing Epo, methods in which the function of the kidney is reduced to reduce the Epo production have been used (Non Patent Literatures 2 to 4). In this method, the majority of the kidney of a rat is removed to induce a decrease in Epo production and anemia associated with deterioration of renal function, which requires skill in, for example, the operative procedure and is a procedure taking a long time. Thus, acquisition of sufficient populations of such animals required much labor.

Epo gene knockout mice develop severe anemia and die in the embryonic stage and, therefore, could not be used in analysis of such a purpose (Non Patent Literature 5). EpoGFP/+ mice were created by knockin of a green fluorescent protein (GFP) gene into the Epo gene to label the Epo-producing cells, and heterozygous mice were crossed to each other to investigate the phenotype of EpoGFP/GFP mice. The phenotype of the EpoGFP/GFP mice was almost the same as that of the Epo gene knockout mice first reported and the EpoGFP/GFP mice died by the 13th day of embryonic life (Non Patent Literature 6).

In order to investigate the functions of Epo in adult mice, conditional knockout mice were produced (Non Patent Literature 6). The mice were produced by rescuing EpoGFP/GFP mice from lethality with an *Escherichia coli* artificial chromosome (bacterial artificial chromosome: BAC) containing an Epo gene carrying a loxP sequence, and embryonic lethality was completely reproduced by crossing with mice broadly expressing Cre recombinase. In addition, expression of drug-induced CRE in the rescued mice caused a decrease in Epo expression in the adult mice. Another laboratory also reported conditional knockout mice produced by directly inserting a loxP sequence into an Epo gene to induce the action of a drug-induced Cre recombinase (Non Patent Literature 7). However, in both experiments, since recombination of the Epo gene in every Epo-producing cell in the body is difficult, the anemia of the mice bred under a usual environment was mild, Epo production induced by anemia induction was recognized, and an increase in reactive hematocrit similar to that of a wild-type was recognized. Furthermore, drug administration has been started after weaning, and analysis can be performed at the point of time when the influence of the drug has completely disappeared after completion of the drug administration. Therefore, in experiments requiring a large number of populations, a large amount of labor and time are necessary. Regarding a HIF2 gene, which is indispensable for hypoxia inducibility control of Epo production, conditional knockout mice were reported (Non Patent Literature 8), and the phenotype thereof was almost the same as that of the Epo gene conditional knockout mice.

In 1993, Maxwell, et al. reported a transgenic mouse produced by inserting the T antigen gene of SV40 virus into an Epo gene fragment of 16 kb, in which homologous recombination of a transgene unexpectedly occurred in the 5' untranslated region of an erythropoietin gene locus (EPO-TAgh) (Non Patent Literature 9). In this mouse, the T antigen mRNA of SV40 is transcribed following a part of the 5' UTR sequence of Epo mRNA. Though the detail of gene construction on the 3' side is unclear, since Epo production detectable by ELISA is present, it is predicted that small amounts of mRNA and protein of the site where the Epo gene is translated are produced. The plasma Epo concentration of the mouse has been reported to be 55±18 pg/mL (wild type: 122±16 pg/mL) under a usual environment and is thus lower than that of the wild type. However, in breeding in a hypoxia chamber, the Epo concentration was 162±25 pg/mL (wild type: 460±39). The concentration significantly increased, although the increase was lower than that of the wild type, and it was judged that the hypoxia inducibility of the Epo gene expression was maintained (Non Patent Literature 10). In the first report, the homozygous mice had a hematocrit of 13.2±3.3% and had severe anemia (Non Patent Literature 9). In the subsequent report on Epo TAg, the hematocrit of homozygous mice was 19.2±0.2% (Non Patent Literature 11). Also in other reports, the values were similar levels (Non Patent Literatures 10, 12, and 13). The hematocrit of EPO-TAgh heterozygote was reported to be 34.4±3.5%, which suggests a possibility that in EpoTAg heterozygote, a material produced from the EPO-TAgh gene locus dominant-negatively acts on the wild-type Epo to cause anemia. EPO-TAgh homozygous mice are used in research on, for example, genetic treatment. In addition, immunological response to mouse Epo is also reported, and it is predicted that the immune system is activated for expressing SV40 TAg having strong immunogenicity (Non Patent Literature 11). It is concerned from these results that too many unclear points remain in the Epo-TAg mouse to use it as a standard of Epo production deficient mouse.

It was reported that Epo-producing cells (renal Epo producing cells: REPs) of the kidney, which is a main organ producing Epo in adults, fibroblast-like cells present so as to surround the proximal tubule and express a neuronal marker, by producing a transgenic mouse, Epo-BAC-GFP-Tg, having a bacterial artificial chromosome (BAC) containing an Epo gene and identifying the Epo-producing cells using both the Epo-BAC-GFP-Tg and Epo (GFP/+) mice (Non Patent Literatures 14 and 15).

Many of past papers regarding the mechanism of controlling Epo production are based on research using a liver cancer-derived cell line, and the characteristics of REPs and the surrounding environment thereof are completely different from those of hepatocytes. In the kidney, there is a possibility that an Epo production-controlling mechanism different from that in the liver is working. The Epo-BAC-GFP-Tg mouse is an excellent experimental animal for analyzing Epo production control in the kidney, but requires treatment, such as induction of anemia by successive blood-removing treatment or breeding in a hypoxia chamber, in actual research. In addition, the anemia induced by such treatment has the disadvantage of a large individual difference.

CITATION LIST

Non Patent Literature

Non Patent Literature 1: Takeda A, Tada T, Shinohara S, Mogi Y, Matsui N. Factors contributing to higher hematocrit levels in hemodialysis patients not receiving recombinant human erythropoietin. American journal of kidney diseases: the official journal of the National Kidney Foundation. 2002; 40:104-109.

Non Patent Literature 2: Gagnon R F, Duguid W P. A reproducible model for chronic renal failure in the mouse. Urological Research. 1983; 11:11-14.

Non Patent Literature 3: Gagnon R F, Gallimore B. Characterization of a mouse model of chronic uremia. Urological Research. 1988; 16:119-126.

Non Patent Literature 4: Garcia D L, Anderson S, Rennke H G, Brenner B M. Anemia lessens and its prevention with recombinant human erythropoietin worsens glomerular injury and hypertension in rats with reduced renal mass. Proceedings of the National Academy of Sciences of the United States of America. 1988; 85:6142-6146.

Non Patent Literature 5: Wu H, Liu X, Jaenisch R, Lodish H F. Generation of committed erythroid BFU-E and CFU-E progenitors does not require erythropoietin or the erythropoietin receptor. Cell. 1995; 83:59-67.

Non Patent Literature 6: Shun Yamazaki, Norio Suzuki, Naoshi Obara, Xiaoqing Pan, Ikuo Hirano, Kou-ichi Jishage, Kurisu Honda, Naoko Minegishi, and Masayuki Yamamoto. Rescue of Erythropoietin-Deficient Mice From Anemia by Complementation with BAC Transgene. Blood (ASH Annual Meeting Abstracts), November 2009; 114: 3614.

Non Patent Literature 7: Zeigler B M, Vajdos J, Qin W, Loverro L, Niss K. A mouse model for an erythropoietin-deficiency anemia. Disease Models & Mechanisms. in press Non Patent Literature 8: Kapitsinou P P, Liu Q, Unger T L, et al. Hepatic HIF-2 regulates erythropoietic responses to hypoxia in renal anemia. Blood. 2010; 116:3039-3048.

Non Patent Literature 9: Maxwell P H, Osmond M K, Pugh C W, et al. Identification of the renal erythropoietin-producing cells using transgenic mice. Kidney Int. 1993; 44:1149-1162.

Non Patent Literature 10: El Hasnaoui-Saadani R, Pichon A, Marchant D, et al. Cerebral adaptations to chronic anemia in a model of erythropoietin-deficient mice exposed to hypoxia. American Journal of Physiology—Regulatory Integrative & Comparative Physiology. 2009; 296:R801-811.

Non Patent Literature 11: Rinsch C, Dupraz P, Schneider B L, et al. Delivery of erythropoietin by encapsulated myoblasts in a genetic model of severe anemia. Kidney Int. 2002; 62:1395-1401.

Non Patent Literature 12: Binley K, Askham Z, Iqball S, et al. Long-term reversal of chronic anemia using a hypoxia-regulated erythropoietin gene therapy. Blood. 2002; 100: 2406-2413.

Non Patent Literature 13: Gruber M, Hu C-J, Johnson R S, Brown E J, Keith B, Simon M C. Acute postnatal ablation of Hif-2{alpha} results in anemia. PNAS. 2007; 104:2301-2306.

Non Patent Literature 14: Suzuki N, Obara N, Yamamoto M, Helmut S, Bernhard Bn. Use of Gene[hyphen (true graphic)]Manipulated Mice in the Study of Erythropoietin Gene Expression. Methods in Enzymology. Vol. Volume 435: Academic Press; 2007:157-177.

Non Patent Literature 15: Obara N, Suzuki N, Kim K, Nagasawa T, Imagawa S, Yamamoto M. Repression via the GATA box is essential for tissue-specific erythropoietin gene expression. Blood. 2008; 111:5223-5232.

SUMMARY OF INVENTION

Technical Problem

It is an object of the present invention to establish an animal model spontaneously developing anemia associated with a decrease in Epo production and to provide an experimental animal system useful in research on the action mechanism of Epo and a new therapeutic approach for a disease state associated with a decrease in Epo production.

Solution to Problem

Conventionally, since Epo gene homozygous deficient mice are embryonic lethal, no adult mice genetically deficient in endogenous Epo production have been obtained. The present inventors investigated rescue of an embryonic lethal mouse by introducing an Epo gene having a partial deletion of the untranslated region into an Epo gene homozygous deficient mouse produced by insertion of a GFP gene. As a result, unexpectedly, some of the rescued mice decreased the Epo production after birth and spontaneously developed severe anemia.

The analytical results of the rescued mice confirmed that almost no endogenous Epo is produced and that the Epo production in the embryonic stage is compensated by a transgene to avoid the embryonic lethality.

That is, the present invention relates to a transgenic non-human mammal spontaneously developing anemia after birth.

In the transgenic non-human mammal, the postnatal blood erythropoietin (Epo) concentration is decreased.

In an embodiment, in the transgenic non-human mammal, the postnatal Epo production in the kidney is suppressed by genetic modification.

The genetic modification includes, for example, an operation involving knockout of an endogenous Epo gene and introduction of a transgene being an extraneous Epo gene of which expression in the kidney is suppressed.

The transgene preferably contains a region from 3.3-kb upstream to 4.5-kb downstream of the transcription start site of the Epo gene.

In another embodiment, in the transgenic non-human mammal, the knockout of the endogenous Epo gene is performed simultaneously with knockin of a reporter gene.

A preferred example of the reporter gene may include a GFP gene.

The non-human mammal is not specifically limited, and preferred examples thereof include mice such as the mice of 458 system shown in Examples.

An example of the transgenic non-human mammal of the present invention may include mice generated from fertilized eggs deposited under accession No. FERM BP-11347.

The present invention also provides a tissue or cells derived from the transgenic non-human mammal and a cell line established from the tissue or the cells.

The present invention also provides a fertilized egg prepared from the transgenic non-human mammal. Examples of the fertilized egg may include fertilized eggs specified by accession No. FERM BP-11347.

The present invention also provides an Epo-producing cell isolated from the transgenic non-human mammal. Examples of the Epo-producing cell include kidney-derived Epo-producing (REP) cells.

Furthermore, the present invention provides a method of generating Epo-producing cells, the method including the following steps of:
(a) creating the above-described transgenic non-human mammal;
(b) isolating a tissue or cells from the transgenic non-human mammal;
(c) detecting cells expressing a reporter gene in the tissue or the cells; and
(d) isolating the cells expressing a reporter gene.

The present invention further provides a method for screening for an Epo production-promoting active material, the method including the following steps of:
(a) bringing a test material into contact with the Epo-producing cells generated by the above-described method;
(b) detecting expression of a reporter gene in the Epo-producing cells; and
(c) selecting a test material having an activity of promoting the expression of a reporter gene compared to a control.

Advantageous Effects of Invention

In the transgenic non-human mammal (such as mouse) of the present invention, the Epo production spontaneously decreases after birth to a level that can be hardly detected. Therefore, the transgenic non-human mammal can be used as an experimental animal system that can ignore the influence of endogenous Epo. The transgenic non-human mammal of the present invention can easily confirm Epo production using the attenuation of GFP fluorescence as an index. Accordingly, the transgenic non-human mammal of the present invention is extremely useful for research on, for example, erythropoietin, regular hematopoiesis and stress hematopoiesis, and activity of Epo other than the hematopoiesis as well as for development of a method of treating diseases, such as renal anemia and chronic anemia, in which Epo is involved.

BRIEF DESCRIPTION OF DRAWINGS

FIG. 5 shows the ratio of each genotype in offspring obtained in the rescue experiment.

FIG. 14 shows blood data of I-Sam (A: 8 to 10 weeks of age, B: 1 year of age).

This specification includes the contents as disclosed in the specification of Japanese Patent Application No. 2011-083664, which is a priority document of the present application.

DESCRIPTION OF EMBODIMENTS

1. Definition

In the specification, the term "Epo(GFP/GFP) mouse" refers to a mouse having a gene Epo(GFP) (FIG. 2) carrying a GFP cDNA sequence and a poly A sequence inserted in the second exon of an Epo gene in a homozygous state. This mouse is also called knockin/knockout mouse. The mouse shows Epo deficiency and expresses GFP at the time of transcription of the Epo gene. This genetic mutation is produced by genetic homologous recombination and a Cre/loxP method (FIG. 2), and the Epo(GFP/+) mouse is the heterozygote thereof.

In the specification, the term "3.3K-Epo-3'" refers to a gene fragment introduced into a fertilized egg at the time of production of a transgenic mouse. The gene fragment includes a region from 3.3-kb upstream to 4.5-kb downstream of the transcription start site of the Epo gene and has a partial deletion in the untranslated region of the fifth exon for distinguishing from the original Epo gene (see FIGS. 1 and 4).

In the specification, the term "transgene" refers to an introduced gene (exogenously introduced gene) possessed by a transgenic mouse and is equivalent to 3.3K-Epo3' in the present invention.

In the specification, the term "reporter gene" refers to a gene that is linked so as to be under the control of a target gene promoter to enable the detection of the promoter activity. In the present invention, the reporter gene is linked so as to be under the control of a promoter of the Epo gene, which is a target gene, such that the Epo gene is knocked out.

The reporter gene may be any gene encoding a reporter protein that can be clearly distinguished from all other proteins which may be produced in the host. Preferably, the cells before transformation do not possess any gene encoding a protein that is the same as or similar to the reporter protein. More preferably, the reporter gene encodes, for example, an enzyme producing a metabolite that can be easily quantitatively measured by a specific reaction with an exogenous substrate. Examples of the reporter gene include a) chloramphenicol acetyltransferase, b) firefly luciferase, c) β-galactosidase, d) secretory alkaline phosphatase, e) green fluorescent protein (GFP), and modifications thereof.

In particular, the green fluorescent protein (GFP) emits fluorescence by itself and is therefore a reporter gene that can be directly quantitatively measured. Furthermore, modifications thereof are commercially available. In the specification, the green fluorescent proteins including modifications thereof are referred to as "GFP".

Figure 1:
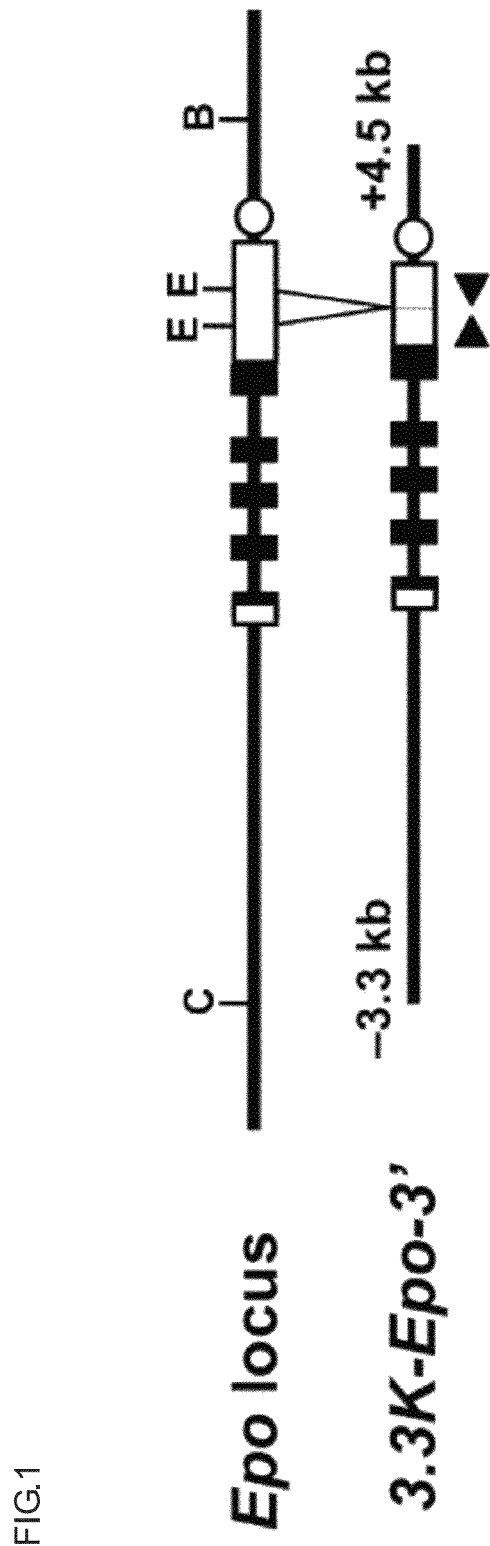
FIG. 1 is a diagram illustrating the assembly of a 3.3K-Epo3' transgene, where the site indicated by two arrowheads is a 310-bp region deleted in the 3' UTR for distinguishing from the endogenous Epo gene.
Figure 3:
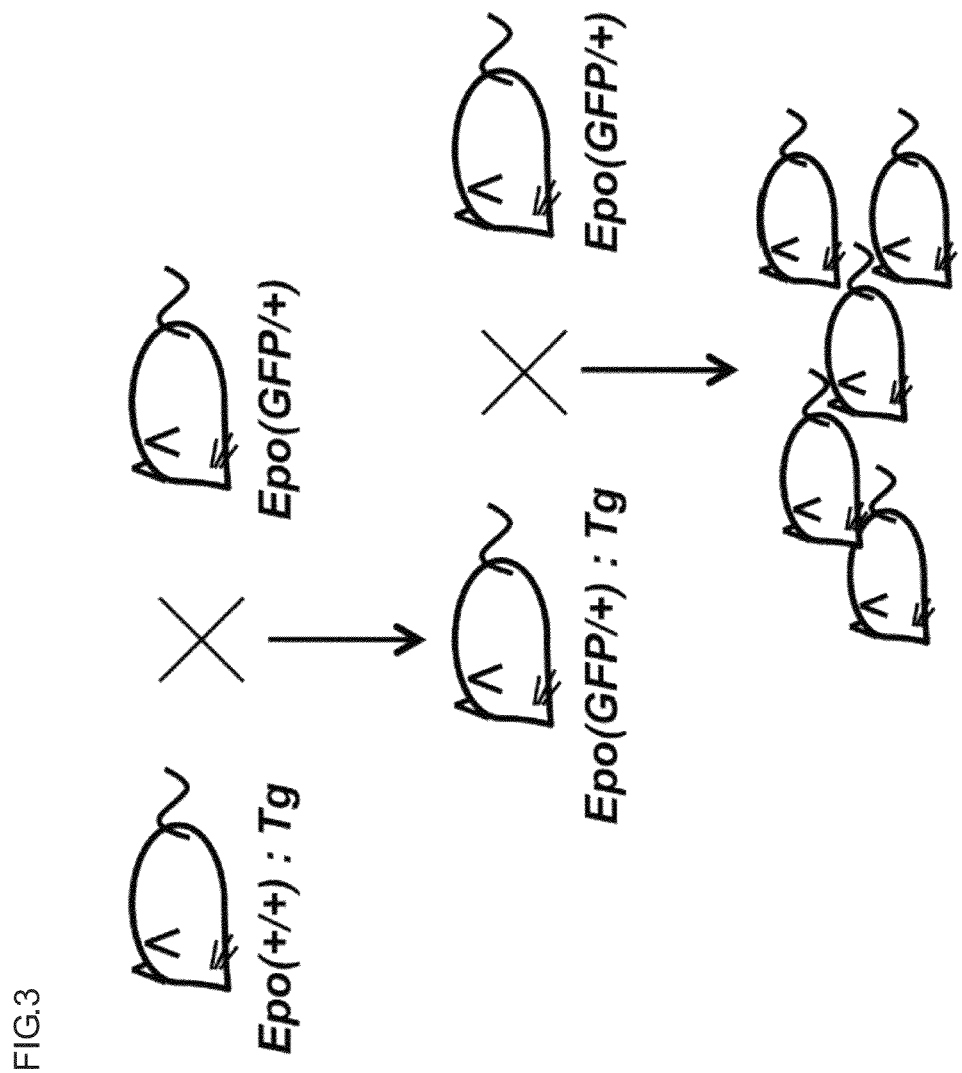
FIG. 3 is a diagram illustrating an experiment of transgenic rescue of Epo(GFP/GFP) mice.

In the specification, the term "3.3K-Epo3' transgenic mouse" refers to a transgenic mouse having a transgene of the 3.3K-Epo3' region and is abbreviated as 3.3K-Epo3' Tg or Tg (see FIGS. 1 and 3).

In the specification, the term "Epo(GFP/GFP):3.3K-Epo3' mouse" refers to an Epo-gene-knockin/knockout homozygous mouse having 3.3K-Epo3' derived from a transgenic mouse. Two lines of three lines do not develop anemia in adults, produce Epo in a normal level under usual breeding conditions, and rather show a tendency of polycythemia (see FIGS. 5 to 7).

In the specification, the term "I-Sam (inherited-super anemic mouse)" or "Epo-deficient GFP anemic mouse" refers to one line of Epo(GFP/GFP):3.3K-Epo3' mouse and is a mouse line having the following characteristics.

Figure 7:
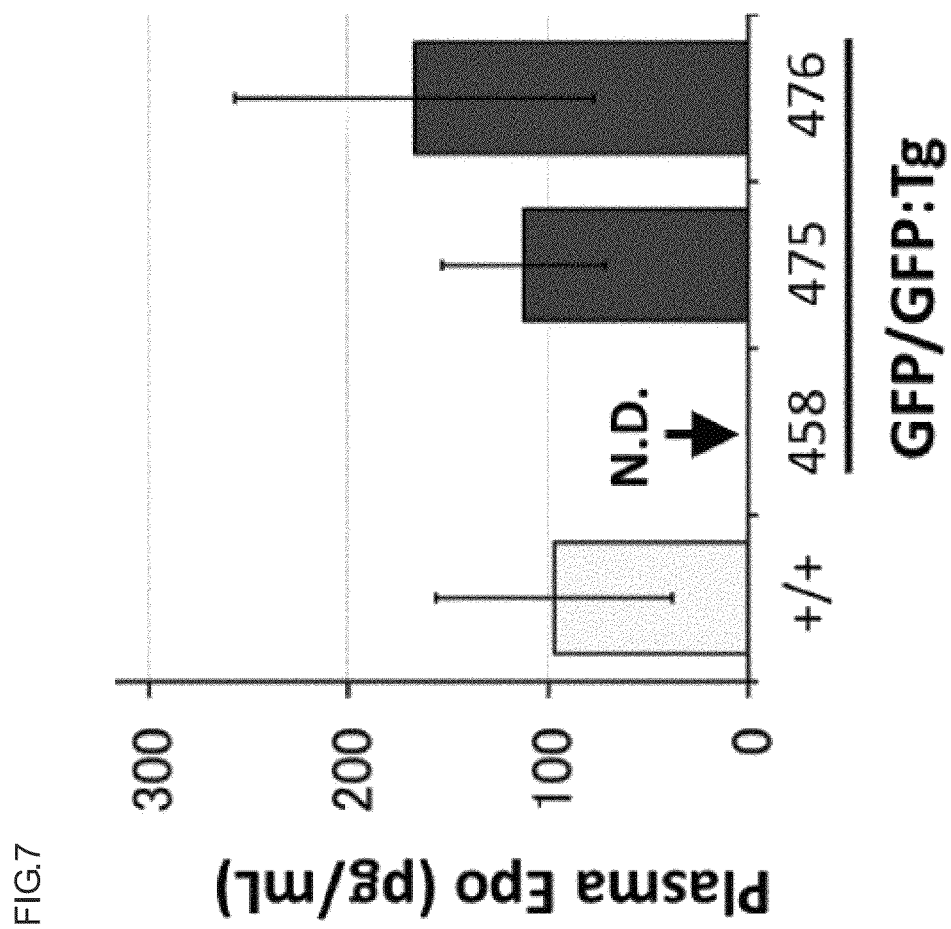
FIG. 7 is a graph showing plasma Epo concentrations (pg/mL) in 8 to 10-week old rescue mice.
Figure 8:
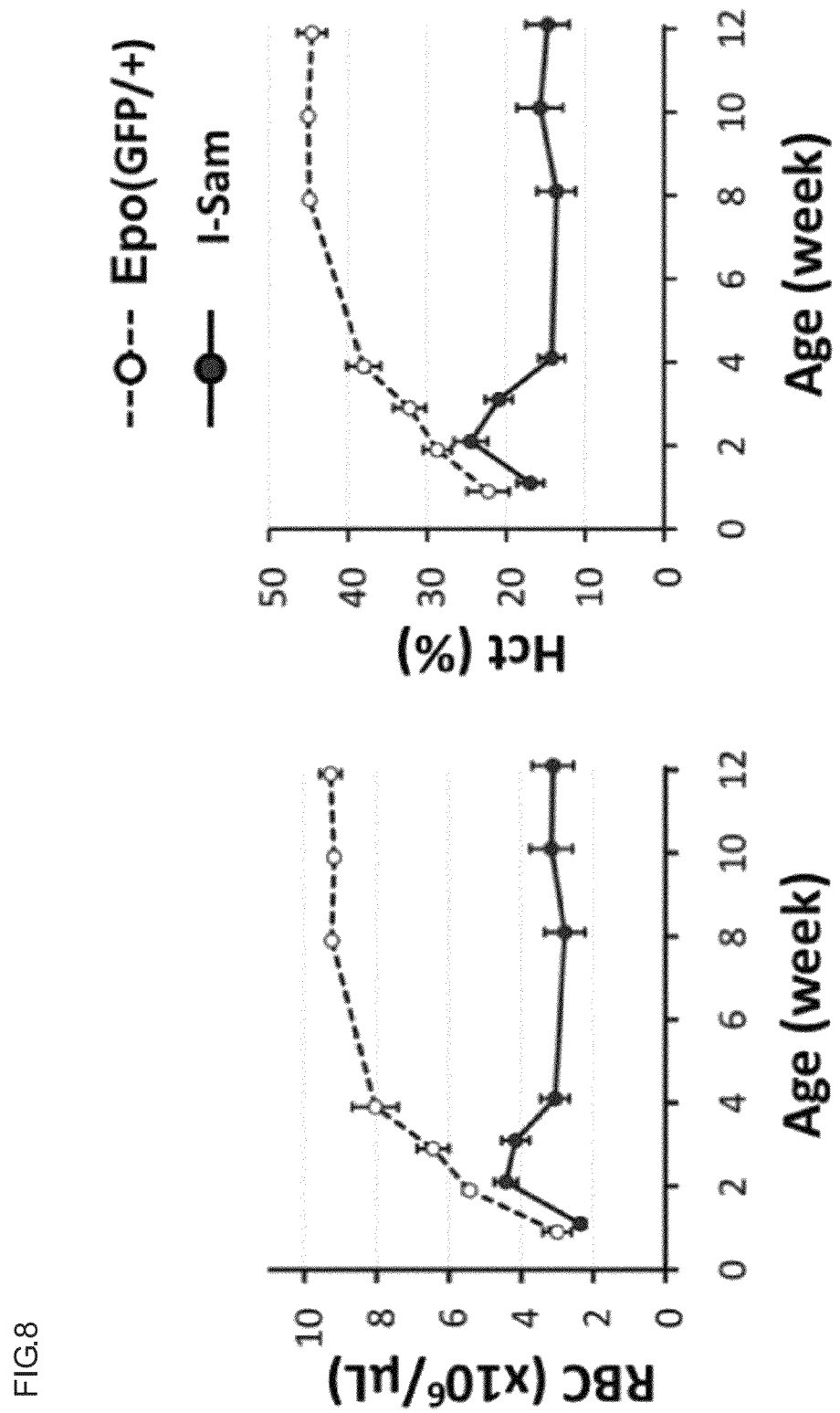
FIG. 8 includes graphs showing time-dependent changes of red blood cell count ($\times 10^6$/μL) and Hct value (%) from 1 to 10 weeks of age, where —○—: control Epo(GFP/+) mice, —●—: I-Sam mice, *P<0.05, and **P<0.005.

The "I-Sam" is born by avoiding the embryonic lethality of Epo(GFP/GFP) (FIG. 5). The plasma Epo cannot be detected or is a very low level 8 to 10 weeks or later after birth to develop severe anemia (FIGS. 7 and 8). The severe anemia due to a decrease in Epo production facilitates transcription from an Epo(GFP) gene, and cells originally having Epo-producing ability are labeled with GFP (see FIGS. 18 to 20).

In the specification, the term "non-human mammal" means a mammal of which examples include primates other than human. In particular, rodents such as rats and mice are easy to deal with, and mice are particularly preferred.

In the specification, the term "anemia" means a lack of red blood cells in blood and various conditions caused thereby. In the transgenic non-human mammal of the present invention, the term means that the blood cell count and/or hematocrit value are reduced by at least 20%, preferably 40%, and most preferably 60% or more, compared to the normal values of the wild type.

2. Transgenic Non-Human Mammal of the Present Invention

The present invention relates to a transgenic non-human mammal spontaneously developing anemia by means of a postnatal decrease in erythropoietin (Epo) production.

2.1 Characteristics

In the transgenic non-human mammal (such as mouse) of the present invention, the Epo production spontaneously decreases after birth to a level that is hardly detected, and thereby anemia is spontaneously developed. Accordingly, the transgenic non-human mammal 2 to 3 months or more after birth can be used as an experimental animal system that can ignore the influence of endogenous Epo. Thus, the transgenic non-human mammal of the present invention is an experimental animal useful for research on erythropoietin, research on regular hematopoiesis and stress hematopoiesis, research on the activity of Epo other than the hematopoiesis, and research on chronic severe anemia and tissue reaction.

The transgenic non-human mammal of the present invention has a knockin Epo-GFP gene in a homozygous state, and the amount of transcription of the Epo gene locus can be detected by the fluorescence of the incorporated GFP. In the transgenic non-human mammal of the present invention, the state of transcription of the Epo gene locus is always in a state of being highly stimulated by means of severe anemia, and cells having Epo-producing ability, including cells having potential ability, in the kidney, the liver, and other tissues are labeled with GFP.

As described above, in the transgenic non-human mammal of the present invention, the transcription of the Epo gene locus is always in a state being highly stimulated, but the postnatal production of the Epo protein itself in the kidney is suppressed by the genetic modification.

In the transgenic non-human mammal of the present invention, before birth, exogenous Epo is produced by the exogenously introduced gene in, for example, the liver and rescues the mammal from lethality by a shortage of Epo or anemia associated therewith.

If research on the control of Epo production using the transgenic non-human mammal of the present invention reveals any control of Epo production by an unknown factor, the factor can be used as a molecular target of a novel treatment. In addition, elucidation of the molecular mechanisms of renal anemia and chronic anemia can be tried using the attenuation of GFP fluorescence as an index by combining experimental models such as renal dysfunction, chronic inflammation, and cancer bearing.

The disease of which treatment can be investigated using the transgenic non-human mammal of the present invention is not limited, and examples thereof include anemia and diseases caused by changes in tissue oxygen partial pressure. The anemia is not limited, and examples thereof include anemia involved in renal failure or an end-stage renal disease, anemia caused by chemical therapy or radiotherapy, anemia due to a chronic disease such as a chronic infectious disease, an autoimmune disorder, rheumatoid arthritis, AIDS, or a malignant tumor, anemia of prematurity, anemia due to hypothyroidism, anemia due to nutritional disturbance such as iron deficiency, and anemia involved in hematological disorder. Examples of the disease caused by changes in tissue oxygen partial pressure include retinopathy of prematurity and ischemic diseases such as cerebral infarction, cerebral embolism, and myocardial infarction.

2.2 "I-Sam (Epo-Deficient GFP Anemic Mouse)"

As an embodiment of the transgenic non-human mammal of the present invention, the above-described "I-Sam (Epo-deficient GFP anemic mouse)" can be exemplified.

The "I-Sam (Epo-deficient GFP anemic mouse)" is a mouse in which cells originally having Epo-producing ability are labeled with a GFP gene knocked-in into the Epo gene. In this mouse, since the transcription of the Epo gene locus is activated by severe anemia, many of the cells having the Epo-producing ability in the whole body express GFP, and, actually, GFP-positive cells in the kidney are considerably increased, compared to those observed in, for example, anemia due to exsanguination. The blood Epo concentration gradually decreases after birth to a level that cannot be detected 8 to 10 weeks after birth or to a very low level.

In general, a mouse homozygously deficient in endogenous Epo production is embryonic lethal and cannot be used in any experiment for an adult. Accordingly, the present invention achieves the purpose by producing a mouse ("I-Sam (Epo-deficient GFP anemic mouse)") that avoids the lethality due to anemia in the embryonic stage by Epo production from a transgene and postnatally loses the Epo production. The present invention utilizes a fact that an introduced transgene does not have transcriptional activity in major Epo-producing tissues, such as the kidney, after birth. In this point, the present invention uses a technique different from the usual method for conditional knockout. This activity of the transgene attributes to both the effects of the gene region into which the transgene has been induced and the location of the insertion site on the chromosome.

The "I-Sam (Epo-deficient GFP anemic mouse)" was found in rescue experiments by induction of Epo gene as a transgene into Epo(GFP/GFP) mice. The activity of the induced transgene causes Epo production in the embryonic stage to avoid the embryonic lethality, but the Epo-producing ability is postnatally lost to develop severe anemia.

The "I-Sam (Epo-deficient GFP anemic mouse)" includes a region of an Epo gene fragment (from 3.3-kb upstream to 4.5-kb downstream). Several lines of transgenic mice were created using the same region, but only one line developed a similar phenotype in rescue experiments. It is therefore believed that the activity of the transgene is affected by the chromosome structure near the insertion site (effect of chromosomal location).

The "I-Sam (Epo-deficient GFP anemic mouse)" does not show a great abnormality in the growth and has a life span that is not highly different from that of wild-type mouse. The reproductive ability does not decrease in both male and female, and mice having the same phenotype can be efficiently obtained by crossing of the "I-Sam (Epo-deficient GFP anemic mouse)". Furthermore, a brood mouse control not developing anemia can be obtained by crossing with an Epo(GFP/+) heterozygous mouse. The "I-Sam (Epo-deficient GFP anemic mouse)" does not show a great abnormality in the shape and tissue image of the kidney and has a normal serum creatinine level. Though cardiac hypertrophy is recognized, it is believed to be secondary hypertrophy due to anemia.

The transcription situation of the Epo gene locus is grasped using the fluorescence of GFP by utilizing an Epo(GFP/GFP) knockin mouse prepared by homologous recombination of the Epo gene with a GFP gene. The Epo production is strongly suppressed under usual conditions, but in the "I-Sam (Epo-deficient GFP anemic mouse)", the transcription of the Epo gene locus is stimulated by anemia due to Epo deficiency in many cells that should originally have Epo-producing ability, and emission of GFP is detected.

The fertilized egg produced by crossing the "I-Sam (Epo-deficient GFP anemic mouse)" with a normal mouse has been deposited with International Patent Organism Depositary, National Institute of Advanced Industrial Science and Technology under accession No. FERM BP-11347 on Mar. 1, 2011.

The anemic mouse of the present invention can be obtained by natural crossing of the mouse obtained from the fertilized egg. More specifically, the fertilized egg has Epo(GFP/+)458Tg+ and Epo(GFP/+)458Tg− at 50:50, stochastically. The Epo and Tg gene both are inherited according to Mendelian inheritance, and the Epo(GFP/GFP)458Tg− is embryonic lethal. Accordingly, in natural mating of mice obtained from the fertilized eggs, crossing of Epo(GFP/+)458Tg+ mice with each other is stochastically 1/5; and crossing of an Epo(GFP/+)458Tg+ mouse with an Epo(GFP/+)458Tg− mouse is stochastically 1/7 and delivers anemic mice.

2.3 Method of Utilizing Transgenic Non-Human Mammal of the Present Invention (1) Experimental Animal System that can Ignore the Influence of Endogenous Epo Analysis of erythropoietin requires an administration experiment using an animal. However, in usual animal experiments, it was difficult to eliminate the influence of endogenous Epo. In addition, analysis in the conventional research on erythropoiesis has been mainly performed for Epo-dependent stress hematopoiesis. In regular hematopoiesis, hematopoiesis proceeds in the presence of a very small amount of Epo, and a possibility of occurrence of Epo-independent erythroid differentiation cannot be denied. Also in investigation by a cell culture system, such as a colony assay, usual animal-derived cells receive stimulation by Epo in the body, but there has been no method for examining the degree of influence by this stimulation. Analysis of embryonic hepatocytes of an Epo gene knockout mouse is possible, but the molecular mechanism of the hematopoiesis in the embryonic stage is highly different from that of the hematopoiesis in an adult. Therefore, there is a demand for analysis using an adult hematopoiesis tissue.

In recent years, unfavorable effects of Epo on cancer and atherosclerotic lesions have been reported with an increase in the number of Epo administration cases. For example, the adaptation criteria of Epo are very strict in the new guideline published by the American Society of Hematology. The ground thereof is only statistical analysis of clinical cases, and the appropriateness thereof needs to be investigated with an experimental animal system. In addition, regarding the use of Epo for protecting tissues, the causal relationship and the mechanism of action need to be confirmed by an animal experiment. The transgenic non-human mammal of the present invention can be suitably used as the experimental animal system.

(2) Experimental Animal System that can be Used in Research on Epo-Producing Ability Inherent in a Tissue and Research on the Path and Material that Stimulate or Suppress the Epo-Producing Ability Drugs that stimulate endogenous Epo production have been being developed, but usual immunostaining is difficult to detect cells producing a small amount of Epo and may cause the problem of specificity depending on the antibody used. Thus, there is no simple method for confirming induction of Epo production at a cellular level.

The formation of a renal anemia condition has been interpreted such that accumulation of uremic materials associated with renal failure impairs Epo production or such that Epo-producing cells are lost by changes in tissue construction such as fibrosis, but the actual state thereof is unclear. In addition, it has been revealed that some dialysis patients do not need Epo, but there is no experimental animal system useful for investigating renal function and Epo production. Furthermore, changes in Epo production and Epo sensitivity are involved in anemia associated with chronic inflammation and cancer bearing conditions, and there is a demand for experimental animals useful for elucidating the mechanism of the changes and finding a method of treatment.

The transgenic non-human mammal of the present invention can be suitably used as such an experimental animal system.

(3) Experimental Animal System that is Useful for Analysis of Reaction Against Chronic Tissue Hypoxia There are only a small number of experimental animals that develop severe chronic anemia. In particular, there are only a small number of experimental animals that keep anemia at almost constant severity even after the growth stage, do not show any inflammatory symptom, and maintain the life span and reproductive ability. There are no experimental animals that can use for analysis of how the tissue hypoxia due to chronic anemia affects the tissue and analysis of the reaction of a tissue such as a hypoxia-responsive system. The transgenic non-human mammal of the present invention can be suitably used as such an experimental animal system.

(4) Screening for Drug that Stimulates Intracerebral Epo Production

In I-Sam, the brain is also in a hypoxia state due to severe anemia, and expression of the GFP gene knocked-in into the Epo gene is observed in astrocytes. Epo produced by glia cells adjacent to nerve cells is predicted to work in a paracrine mode without being mediated by the cerebrovascular barrier, and it is possible to screen for a drug that stimulates the intracerebral Epo production using I-Sam by, for example, experiments on ischemia/reperfusion of the nervous system on the assumption of treatment of, for example, cerebral infarction. Systemic administration of Epo has a possibility of increasing hemoglobin and raising the consistency of blood to lead to recurrence of cerebral infraction, but the possibility is low in a drug that specifically stimulates intracerebral Epo production. Accordingly, a screening system using I-Sam is useful for searching a safe and effective novel therapeutic agent for cerebral infarction.

3. Epo-Producing Cells of the Present Invention 3.1 Epo-Producing Cells

In the Epo-producing cells isolated from the transgenic non-human mammal of the present invention, the activation of Epo expression can be easily detected with a reporter gene. Therefore, the Epo-producing cells of the present invention can be used in, for example, research on the mechanism of controlling Epo production and screening for an Epo production-promoting active material described below.

The Epo-producing cells are not specifically limited as long as they are derived from a tissue or an organ that produces Epo, and examples thereof may include cells derived from, for example, kidney and liver. In particular, kidney-derived Epo-producing cells (renal Epo producing cells: REPs) are preferred.

3.2 Method of Preparing Epo-Producing Cells

The Epo-producing cells of the present invention can be prepared by, for example, (a) creating a transgenic non-human mammal through knockout of an endogenous Epo gene performed simultaneously with knockin of a reporter gene and through introduction of a transgene that is an exogenous Epo gene of which expression in the kidney is suppressed, (b) isolating a tissue or cells from the transgenic non-human mammal, (c) detecting cells expressing a reporter gene in the tissue or cells, and (d) isolating the cells expressing a reporter gene.

Examples of the reporter gene include chloramphenicol acetyltransferase, firefly luciferase, β-galactosidase, secretory alkaline phosphatase, GFP, and modified GFP. Among them, GFP and modified GFP are preferred.

In the present invention, the reporter gene is linked such that the Epo gene is knocked-out under the control of the Epo gene promoter.

3.3 Method for Screening for an Epo Production-Promoting Active Material

It is possible to screen for an Epo production-promoting active material using the Epo-producing cells of the present invention. Such a screening method can be implemented by, for example, (a) bringing a test material into contact with the Epo-producing cells generated by the above-described method, (b) detecting the expression of a reporter gene in the Epo-producing cells, and (c) of selecting the test material that promotes the expression of a reporter gene through comparison with a control.

The Epo production-promoting active material selected by screening is useful as a candidate of the therapeutic agent for the anemia associated with a decrease in Epo production or the diseases caused by changes in tissue oxygen partial pressure.

EXAMPLES

The present invention will now be specifically described by examples, but is not limited to these examples.

Example 1

A decrease in Epo production associated with, for example, renal failure causes severe anemia. This is obvious from that anemia is dramatically improved by Epo administration to renal failure patients. However, whether all of erythropoiesis in adults are Epo dependent or not is unclear and was therefore investigated.

1. Experiment and Method:
1.1 Establishment of Rescue Mouse (I-Sam)
(1) 3.3K-Epo3' Transgenic Mice The region from 3.3-kbp upstream to 4.5-kbp downstream of the transcription start site of a mouse erythropoietin (Epo) gene was cloned, and a region of 310-bp in the 3' UTR was deleted for distinguishing from the endogenous Epo gene (FIG. 1: the site indicated by two arrowheads). This transgene was microinjected into mouse fertilized eggs to establish independent different 10 systems of 3.3K-Epo3' transgenic mice.

(2) Epo(GFP/+) Mice

Figure 2:
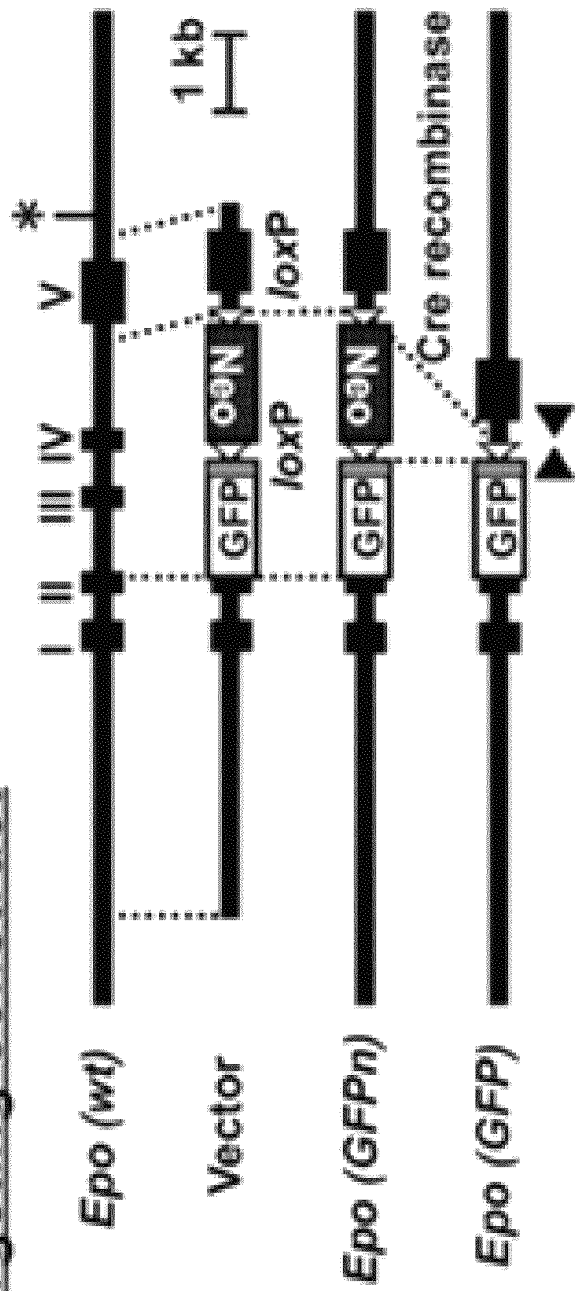
FIG. 2 is a diagram illustrating a targeting construct, where the second to fourth exons of the Epo gene are substituted by an EGFP (Clontech Laboratories, Inc.) gene; and Epo(wt): wild-type Epo gene locus, Epo(GFPn): Epo gene locus in the state targeted by a targeting vector, and Epo(GFP): Epo gene locus finally carrying a knocked-in GFP.

In order to establish mutation mice having GFP cDNA in the Epo gene locus, a targeting vector having EGFP cDNA, an MC1-Neo cassette adjacent to the loxP sequence (Morita M. et al., EMBO J., 2003, 22(5): 1134-1146), an MC1-DT3 cassette (Takahashi S. et al., M. J. Biol. Chem., 1997, 272 (19): 12611-12615), and a 129SV mouse-derived genome sequence (Imagawa S, et al., Int. J. Hematol., 2002, 75(4): 376-381) was prepared. In the targeting vector, the second to fourth exons of the Epo gene are substituted by an EGFP (Clontech Laboratories, Inc.) gene (FIG. 2).

Four independent germlines of chimera mice were created by injecting mutated ES cells prepared by homologous recombination of the targeting vector (genotype Epo (GFPn/+)) into blastocysts of C57BL/6 mice. In order to cut out the MC1-Neo cassette, a genotype Epo(GFP/+) mouse was prepared by crossing a genotype Epo(GFPn/+) heterozygous knockin mouse with an Ayul-Cre transgenic mouse expressing Cre recombinase in the germ line. The crossing of the Epo(GFP/+) mouse was repeated to obtain Epo(GFP/GFP) of which Epo gene is knocked-out in a homozygous state. As in the past reports, the Epo(GFP/GFP) mice developed severe anemia and died around on the 13th day of embryonic life.

(3) Transgenic Rescue of Epo(GFP/GFP) Mice

Crossing of a 3.3K-Epo3' transgenic mouse with an Epo (GFP/+) mouse was repeated for inspecting whether an Epo (GFP/GFP):3.3K-Epo3' mouse (rescue mouse) can be obtained or not (FIG. 3).

The genomic DNA was extracted from offspring and was subjected to three types of PCR. That is, the knockout allele was detected (indicated by two arrowheads in FIG. 2) using an Epo-GFP primer set, the deleted region in the transgene was detected using a 3.3Epo-Tg primer set (same as above), and the sequence (indicated by symbol * in FIG. 2) specific to the wild-type Epo gene allele was detected using a wild-type primer set (same as above). The region deleted in the transgene was observed as a PCR product shorter than the wild-type Epo gene allele or the knockout allele (bands indicated by an arrowhead in FIG. 4).

Figure 4:
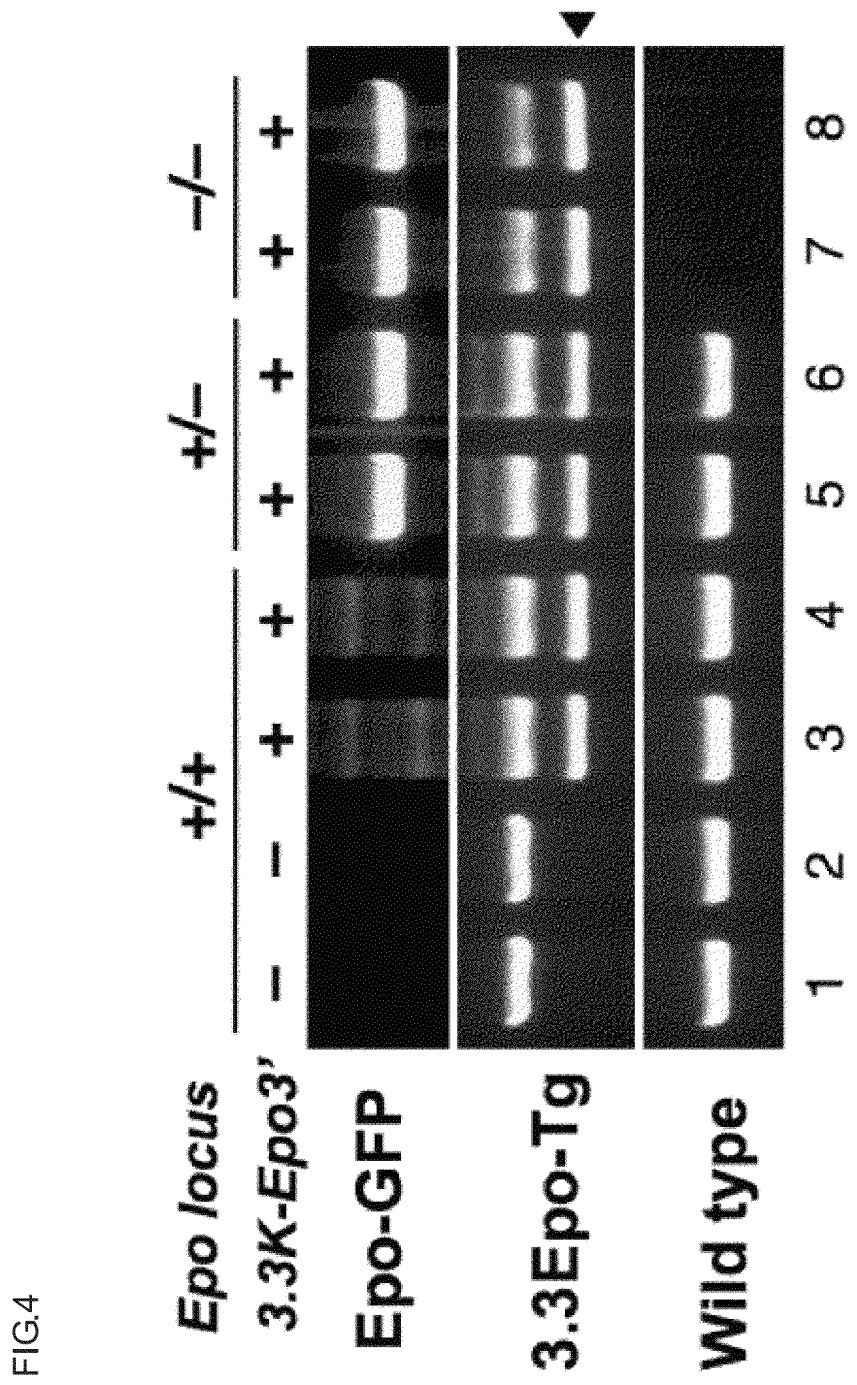
FIG. 4 is a diagram illustrating PCR genotyping of offspring obtained in the rescue experiment, where Epo-GFP (knockout allele: corresponding to the region indicated by two arrowheads in FIG. 2), 3.3Epo-Tg (the band indicated by an arrowhead, the deleted region in the transgene: corresponding to the region indicated by two arrowheads in FIG. 1), and Wild type (sequence specific to the wild-type Epo gene allele: corresponding to the site indicated by a symbol * in FIG. 2).

The sequences of the primers used are shown below:
Epo-GFP primer set:

(SEQ ID NO: 1)
GFP-cs: actctcggcatggacgagctg (SEQ ID NO: 2)
Epo-RTR: gtgagtgttcggagtggagcagg 3.3Epo-Tg primer set:

(SEQ ID NO: 3)
Epo-5UTRs: acaggaaggtctcacatagcc (SEQ ID NO: 4)
Epo-s5: tacagctaggagagttgtgtgg Wild-type primer set:

(SEQ ID NO: 3)
Epo-5UTRs: acaggaaggtctcacatagcc (SEQ ID NO: 5)
Epo-B6as: tggggaaacccccatgagatc In lanes 7 and 8, the sequence specific to the wild-type Epo gene allele was not observed, and only the regions deleted in the knockout allele and the transgene were observed. This result confirms that Epo(GFP/GFP):3.3K-Epo3' mouse (rescue mouse) is born (FIG. 4: lanes 7 and 8).

(4) Ratio of Each Genotype in Offspring Obtained in Rescue Experiment

The ratio of each genotype in the resulting offspring was investigated by a rescue experiment as in above using transgenic mice of four different systems. As a result, it was confirmed that Epo(GFP/GFP):3.3K-Epo3' (rescue mice) are born according to an expected value in three systems (FIG. 5). These rescue mice can be crossed, and the resulting offspring was also born according to an expected value.

1.2 Characteristics of Rescue Mouse (I-Sam)
(1) Hematocrit Value (Hct value) (%)

Figure 6:
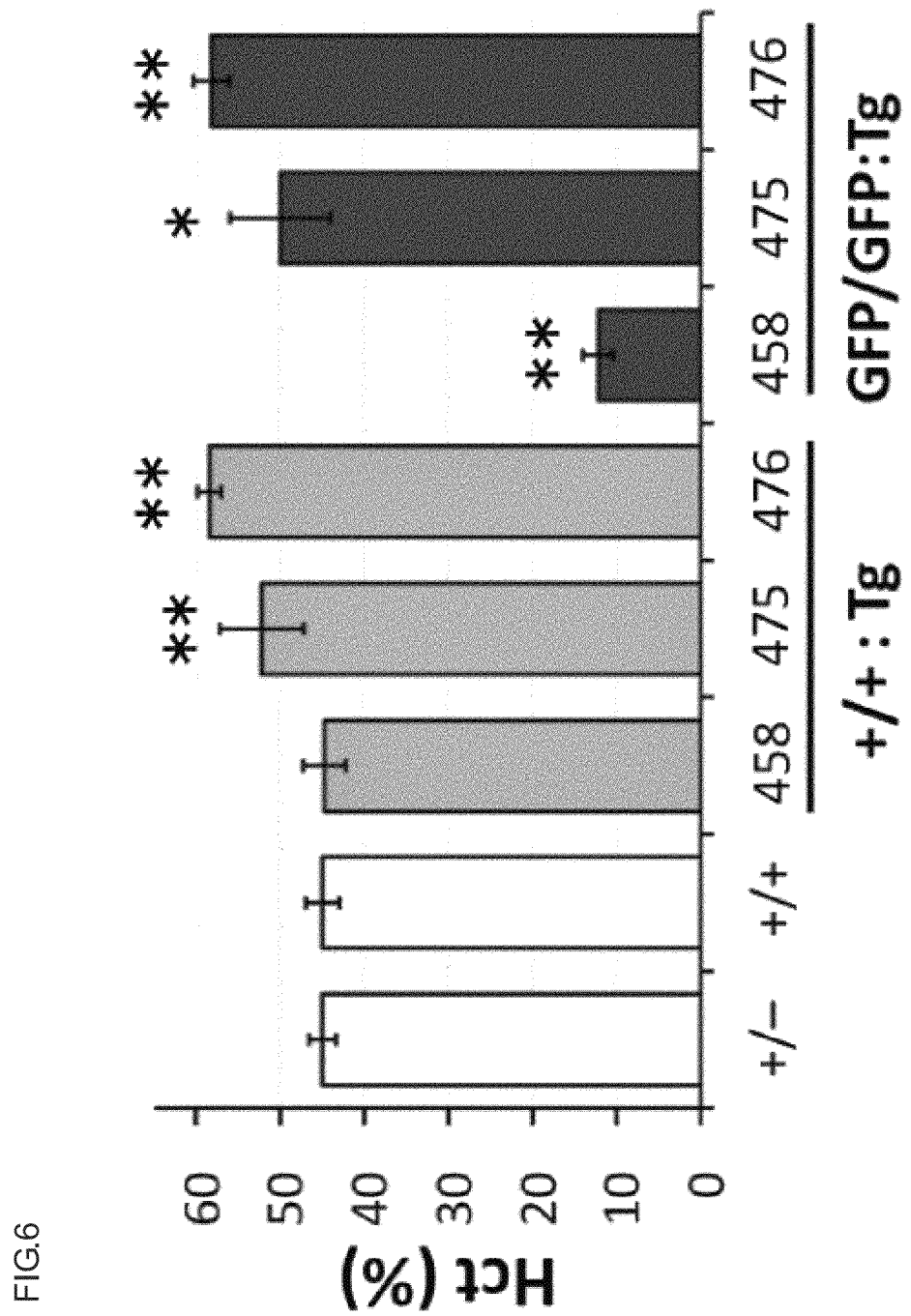
FIG. 6 is a graph showing Hct values (%) in 8 to 10-week old rescue mice, where *P<0.05 and **P<0.005 (comparison with Epo(−/+) mice).

The Hct values (%) of 8 to 10-week old rescue mice were investigated. The rescue mice of 458 system developed severe anemia, but the rescue mice of other systems developed polycythemia (FIG. 6). Hereinafter, the rescue mice of the 458 system are referred to as I-Sam (inherited-super anemic mouse).

(2) Plasma Epo Concentration (pg/mL)

The plasma Epo concentrations (pg/mL) of 8 to 10-week old rescue mice were measured with an Epo ELISA kit (Quantikine, Mouse/Rat Epo ELISA kit (R&D systems, Inc.)). The Epo concentration of I-Sam was lower than the detection limit, but those in rescue mice of other systems were the same as or higher than that of the control, Epo(GFP/+) (FIG. 7).

(3) Time-Dependent Changes of Red Blood Cell Count ($\times 10^6/\mu L$) and Hct value (%)

Time-dependent changes of red blood cell count ($\times 10^6/\mu L$) and Hct value (%) were investigated from 1 to 10 weeks of age (FIG. 8). In Epo(GFP/+) as a control, the amount of red blood cells increased with growth from the anemic condition after birth. On the other hand, though I-Sam showed mild anemia compared to the control until 2 weeks of age, the amount of red blood cells gradually decreased after 3 weeks of age in I-Sam and was kept at a constant anemia level.

(4) Plasma Epo Concentrations from 1 to 4 Weeks of Age

Figure 9:
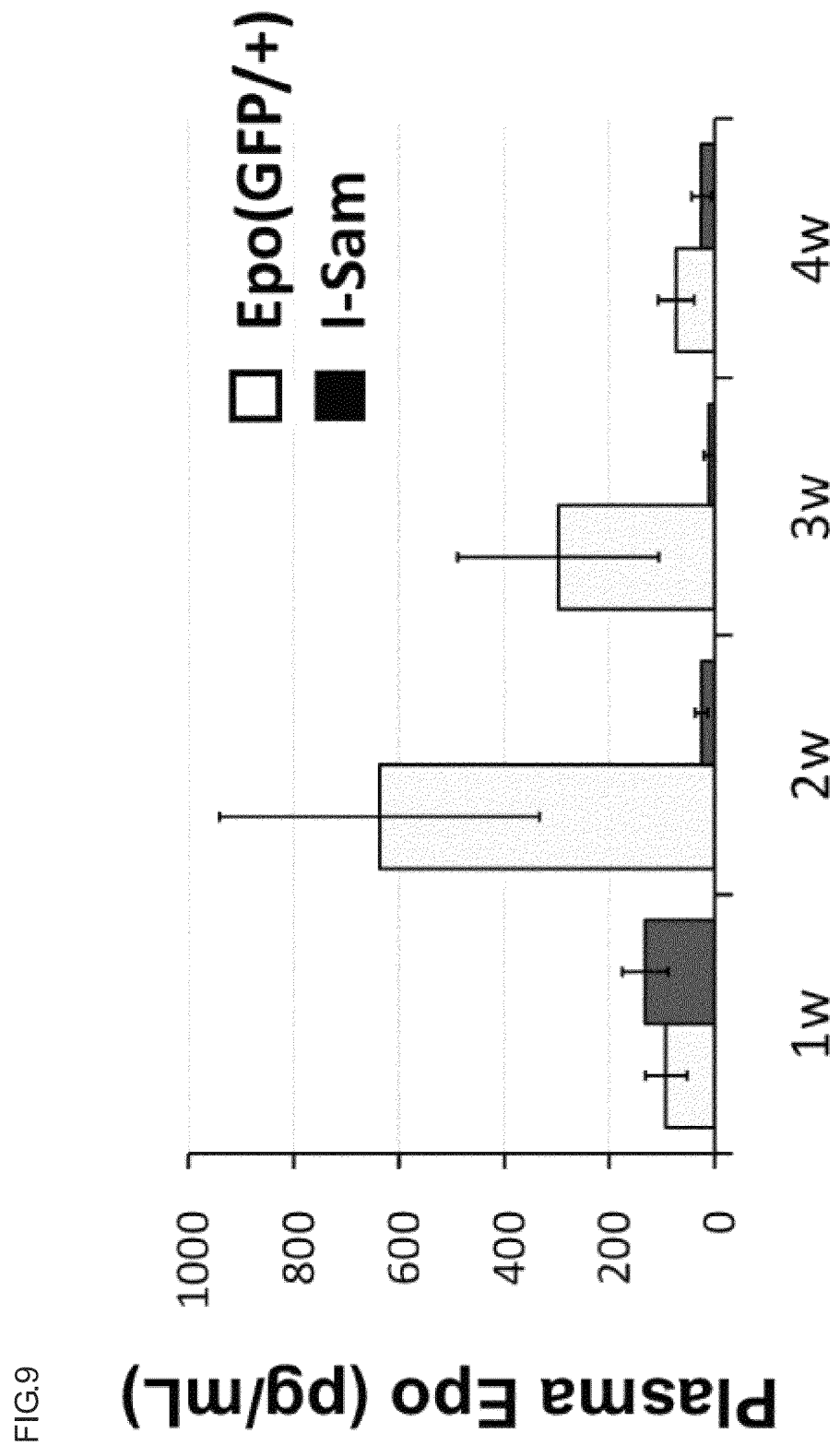
FIG. 9 is a graph showing plasma Epo concentrations from 1 to 4 weeks of age, where left: control Epo(GFP/+) mice, and right: I-Sam mice.

I-Sam and Epo(GFP/+) were compared for plasma Epo concentrations from 1 to 4 weeks of age (FIG. 9). The plasma Epo concentration in I-Sam was the same level as that in Epo(GFP/+) as a control at 1 week of age, but decreased to a detection limit level after 2 weeks of age.

(5) Epo Expression Level in Liver at 1 Week of Age

Figure 10:
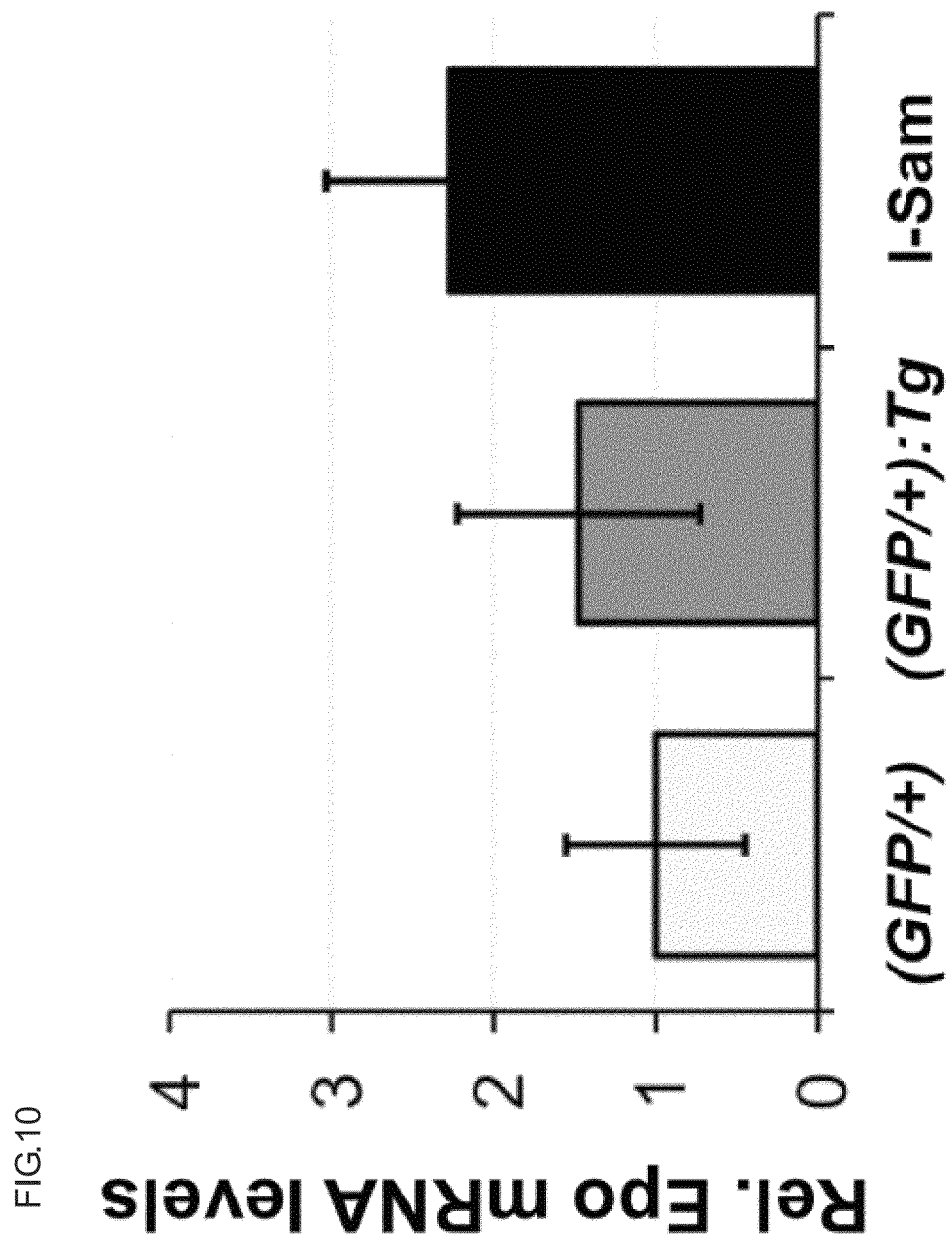
FIG. 10 is a graph showing Epo expression levels in the liver at 1 week of age, where the left in the graph: control Epo(GFP/+), center: Epo(GFP/+):Tg mice, and right: I-Sam mice.

Epo mRNA level was quantitatively measured using a primer detecting both the endogenous Epo mRNA and the 3.3K-Epo3' transgene-derived Epo mRNA (FIG. 10). The Epo mRNA was detected in the liver of I-Sam, and the expression level thereof was higher than that of the control Epo (GFP/+).

(6) Observation of Embryo (The 13th Day of Embryonic Life)

Figure 11:
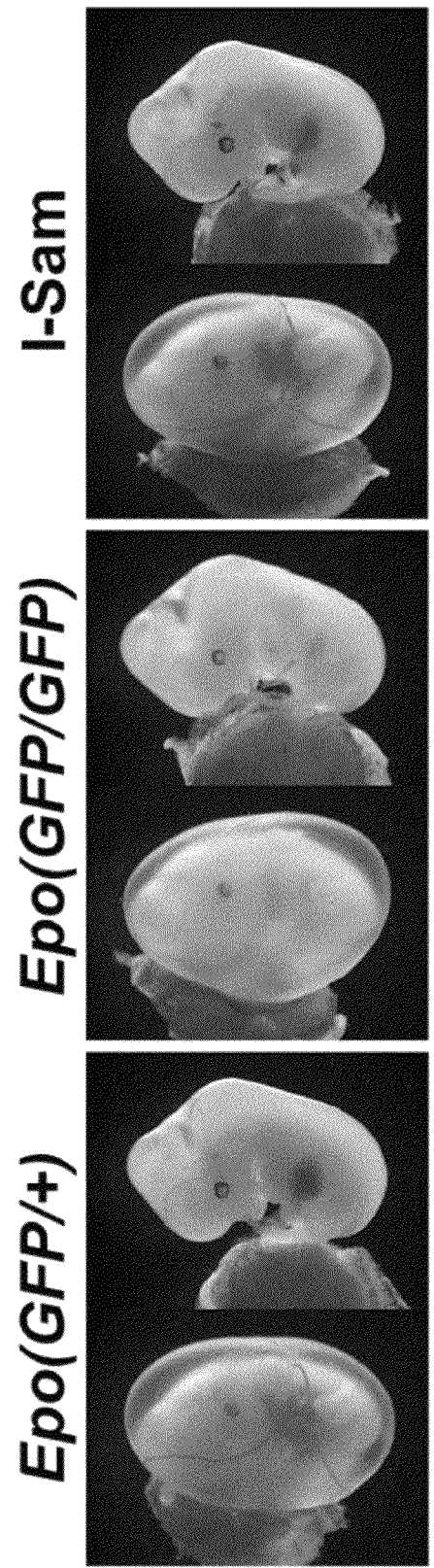
FIG. 11 includes photographs showing the observations of embryo on the 13th day of embryonic life, where left: control Epo(GFP/+) mice, center: Epo(GFP/GFP) mice, and right: I-Sam mice.

FIG. 11 shows photographs of embryos on the 13th day of embryonic life. Epo(GFP/GFP) causes hematopoietic disorder in the embryonic liver and thereby develops severe anemia to die around the 13th day of embryonic life. On the other hand, it was observed that I-Sam recovers hematopoiesis of the embryonic liver to show the same observations as in the control Epo(GFP/+).

Figure 12:
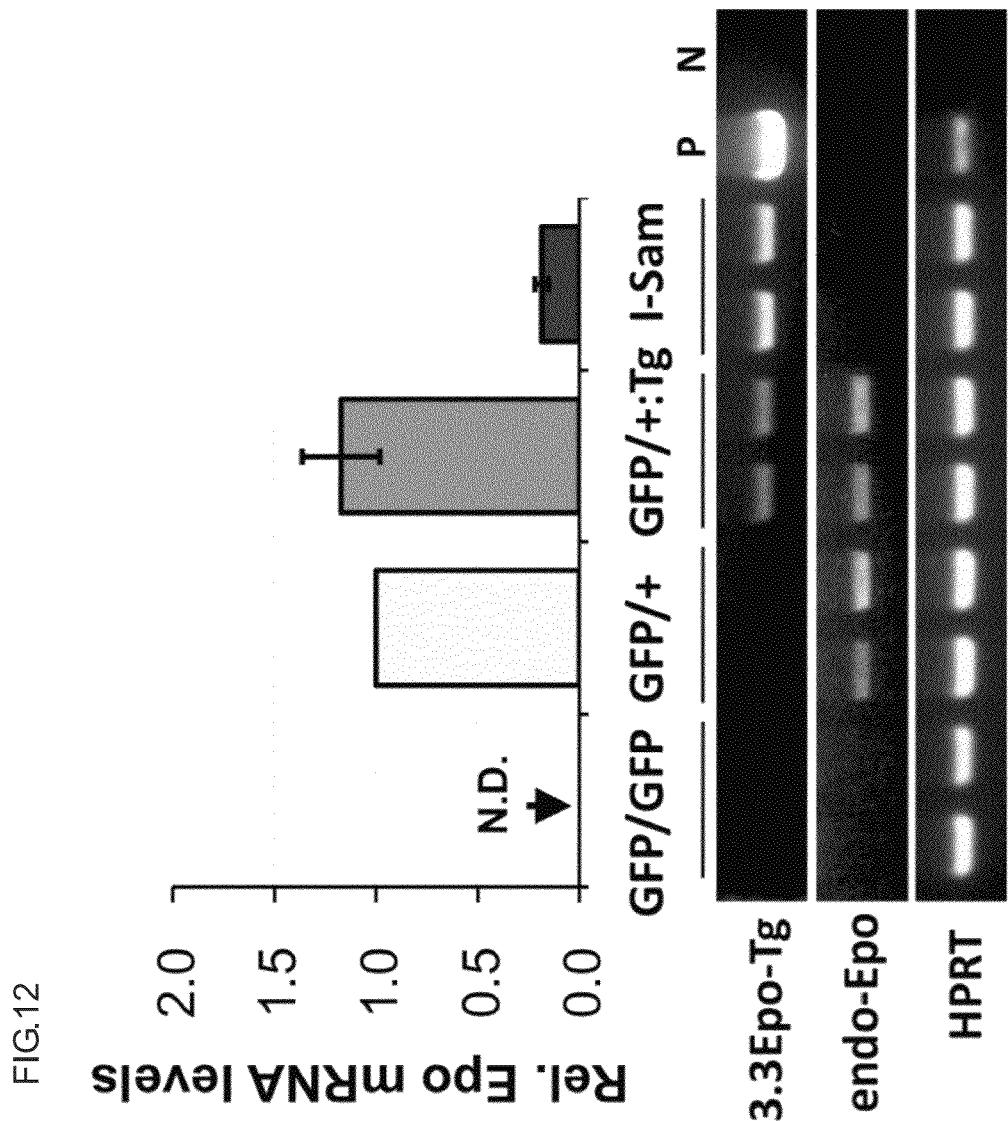
FIG. 12 is a graph showing Epo expression levels in embryonic mouse livers on the 13th day of embryonic life, where the bars show, from the left, Epo(GFP/GFP) mice, control Epo (GFP/+) mice, Epo(GFP/+):Tg mice, and I-Sam mice; 3.3Epo-Tg (the deleted region in the transgene: corresponding to the region indicated by two arrowheads in FIG. 1), endo-Epo (endogenous Epo), and HPRT (housekeeping gene); and *P<0.05 and **P<0.005.

In observation of the Epo expression level in the embryonic liver on the 13th day of embryonic life, Epo mRNA was detected in the embryonic liver of I-Sam, and the expression level thereof was about 20% that of the control Epo(GFP/+) (FIG. 12). This Epo mRNA expressed in the embryonic liver of the I-Sam was recognized to be derived from the 3.3K-Epo3' transgene using a primer that distinguishes the Epo mRNA from endogenous Epo mRNA.

(7) Survival Rate of I-Sam

Figure 13:
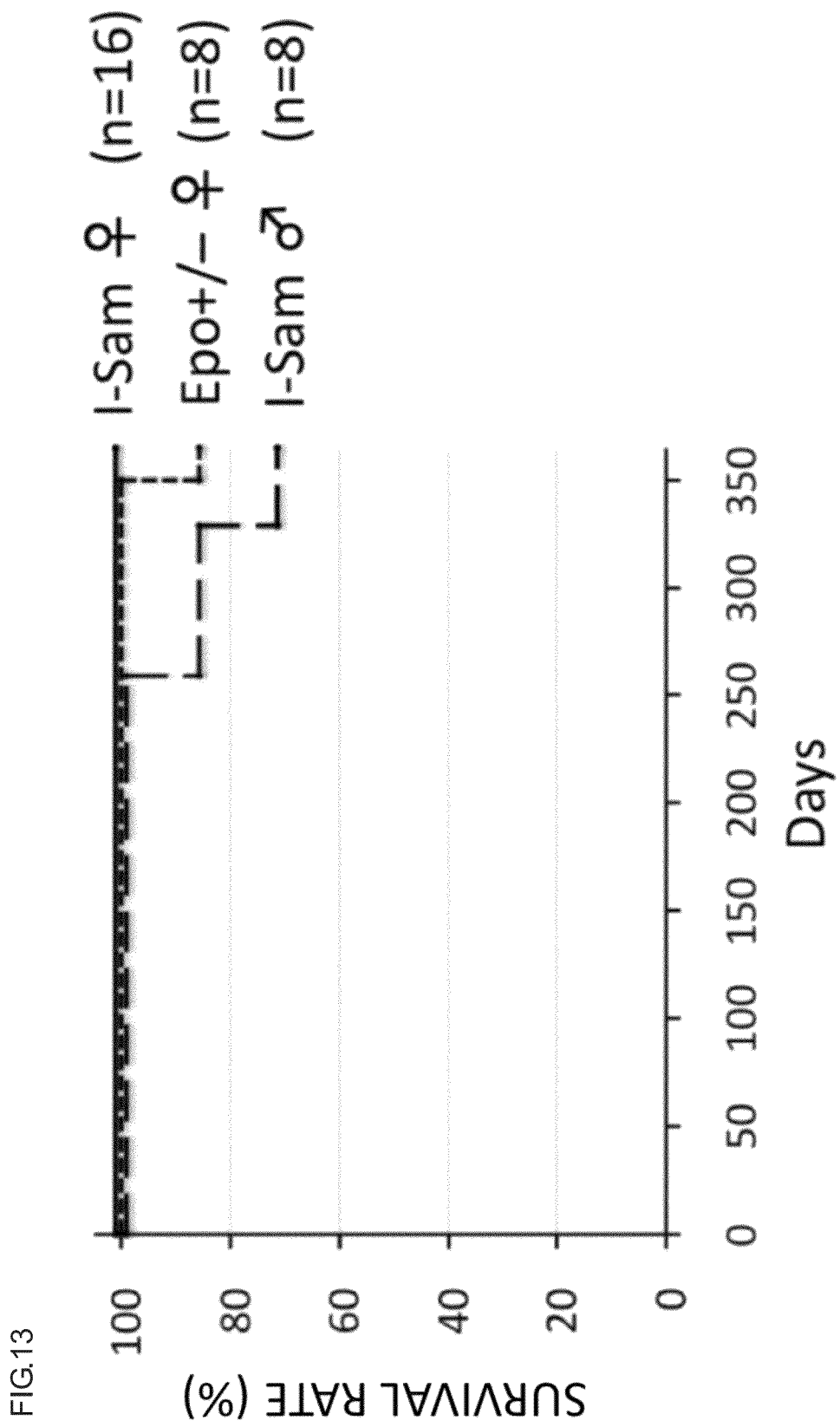
FIG. 13 is a graph showing survival rates of I-Sam.

There was no significant difference between the survival rates of I-Sam and Epo(GFP/+) mice (FIG. 13).

(8) Blood Data of I-Sam

Blood data of I-Sam show that all of the blood cell (RBC) count, hemoglobin (HGB) concentration, and hematocrit (HCT) value 8 to 10 weeks after birth were lower than those of the control Epo(GFP/+) and that I-Sam developed severe anemia. Even 1 year after birth, these values did not change to keep the same anemic condition (FIG. 14).

(9) Copy Number of Epo Gene

Figure 15:
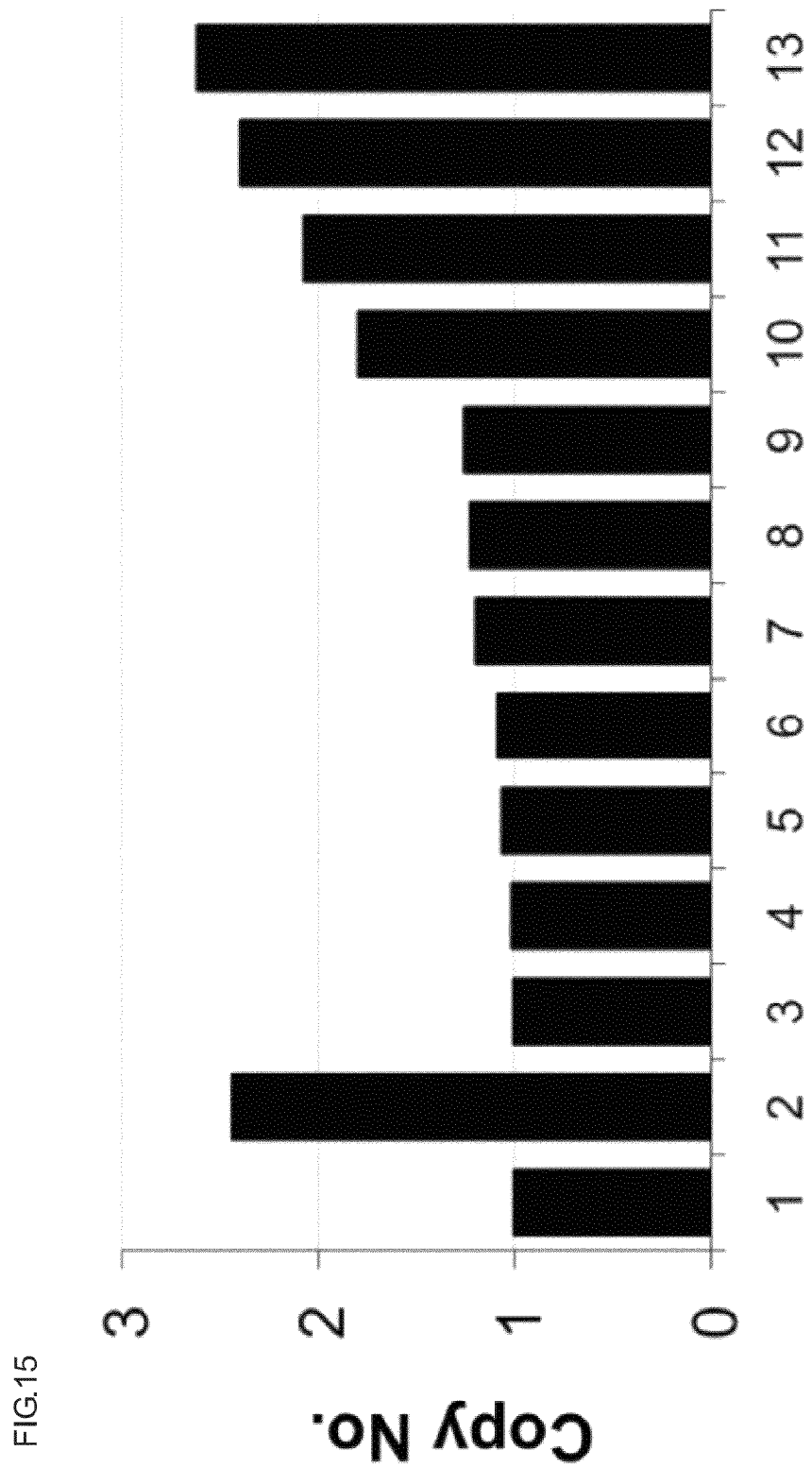
FIG. 15 is a graph showing copy numbers of the Epo gene, where 1: Epo(−/−), 2: Epo(+/+), 3 to 9: I-Sam (hemizygote) having one copy of a transgene (Tg), and 10 to 13: I-Sam (homozygote) having two copies of the Tg.

The copy number of the fourth exon portion of the Epo gene was quantitatively measured by real-time PCR using the genomic DNA (FIG. 15). As an internal standard, a Gata2 gene located on another chromosome was used. When the copy number of Epo(+/−) is defined as one, two copies of Epo(+/+) were confirmed (bars 1 and 2 in the graph). In crossing of I-Sam with each other, I-Sam having one copy of the transgene (Tg) (hemizygote, bars 3 to 9 in the graph) and I-Sam having two copies of the Tg (homozygote, bars 10 to 13 in the graph) were born.

Figure 16:
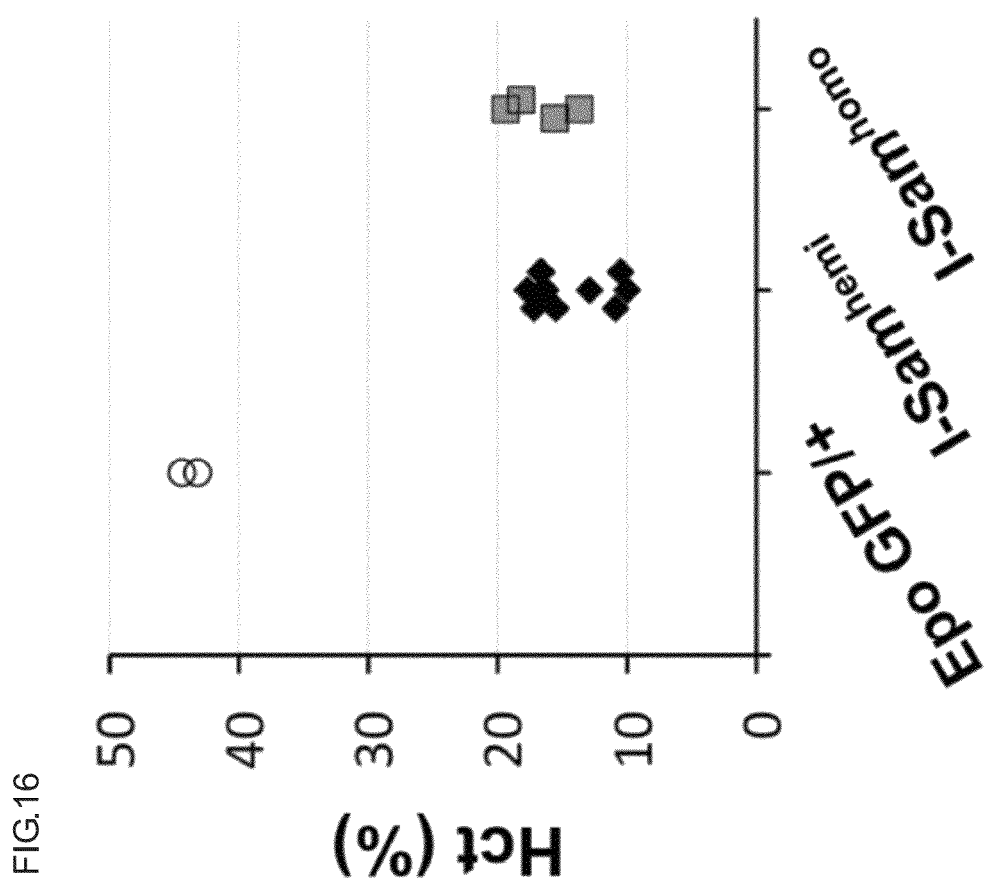
FIG. 16 is a graph showing Hct values (%) of homozygous I-Sam, where I-Samhomo: I-Sam having two copies of a transgene (Tg), and I-Samhemi: I-Sam having one copy of the Tg.

The Hct value (%) of homozygous I-Sam was measured, and it was confirmed that homozygote (I-Samhomo) at 24 weeks of age developed severe anemia as in hemizygote (1-Samhemi) (FIG. 16).

(10) Plasma Epo Concentration of I-Sam

Figure 17:
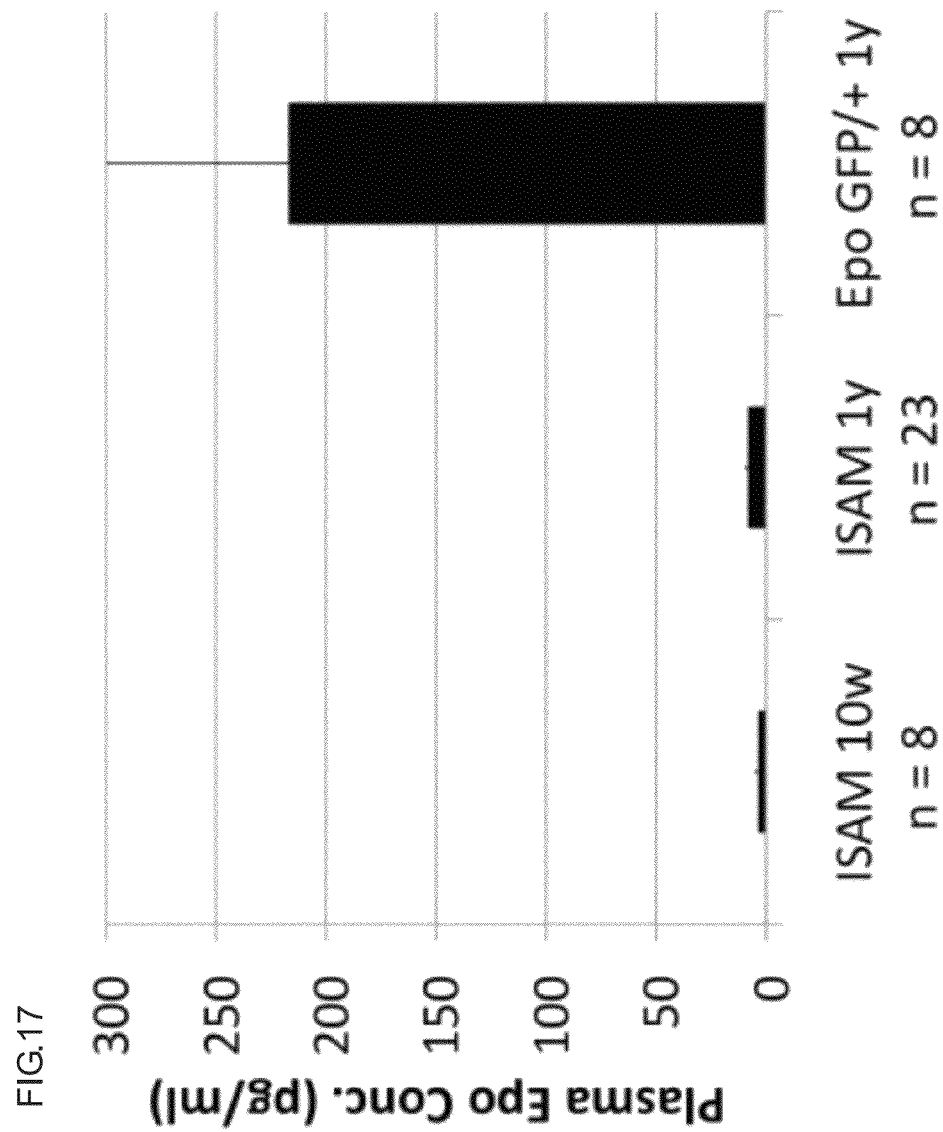
FIG. 17 is a graph showing plasma Epo concentrations.

The plasma Epo concentrations of I-Sam were measured in mice 10 weeks and 1 year after birth (FIG. 17).

2. Results

Anemia was recognized in I-Sam 1 week after birth. Then, the blood cell count and hematocrit value in I-Sam slightly increased 2 weeks after birth, but then decreased, whereas those in wild-type mice increased by about two times. 8 to 10 weeks after birth, the Hct value was 14.2±3.0% (8 to 10 weeks after birth, the Hct value of the control at the same stage was 44.2±2.3%) to develop severe anemia (FIGS. 8 and 14). Similarly, the plasma Epo concentration was the same as that of the control Epo(GFP/+) 1 week after birth, but the Epo concentration decreased 2 weeks after birth, whereas that of the control increased. The decreased concentration was kept after that (FIG. 9). The data 10 weeks after birth is shown (FIG. 17). This phenotype was not improved and also was not worsened even in I-Sam 1 year after birth.

Since the plasma Epo concentration of I-Sam 1 week after birth was the same as or higher than that of the control, the expression of Epo mRNA in the liver, which is the major Epo-producing organ in the embryonic stage, was investigated by quantitative RT-PCR, and a tendency for the expression to increase more in I-Sam than in the control was observed (FIG. 10).

Epo(GFP/GFP) mice developed anemia on the 13th day of embryonic life, and the liver thereof was white. Around this stage, Epo(GFP/GFP) mice became embryonic lethality. On the other hand, in I-Sam, the red of hemoglobin was recognized in the liver as in heterozygous Epo(GFP/+), and red blood cells were also recognized in the vessel (FIG. 11). I-Sam was born according to the Mendel's rule to avoid embryonic lethality (FIG. 5).

The expression of Epo mRNA in the liver on the 13th day of embryonic life was investigated by quantitative RT-PCR, and it was confirmed that the expression was about 20% of that of the heterozygous Epo(GFP/+) and was derived from the transgene (FIG. 12).

The fertilized egg produced by crossing of I-Sam with a normal mouse was deposited with International Patent Organism Depositary, National Institute of Advanced Industrial Science and Technology under accession No. FERM BP-11347 on Mar. 1, 2011.

Example 2

Though the Epo-producing organs in adults are the kidney and the liver, there also are reports on Epo production in other organs. Accordingly, based on a prediction that severe anemia is developed in I-Sam mice and that almost the highest transcriptional activity of hypoxia-responsive Epo gene is being induced in each tissue, the Epo expressions and GFP expressions were investigated for three mice of each of I-Sam and Epo(GFP/+) 12 weeks after birth.

1. Experiment and Method (1) Epo Expression

RNA was extracted from each organ of three mice of each of I-Sam and Epo(GFP/+) at 12 weeks of age. After reverse transcription, the Epo mRNA levels were measured by quantitative PCR. In Epo(GFP/+), the Epo expression in the kidney is recognized to be low, but is highly induced by anemia (Ane, Kid: defined to be 100).

(2) GFP Expression

RNA was extracted from each organ of each of the three mice, reverse transcription was performed, and then GFP mRNA levels were quantitatively measured by real-time PCR. Frozen sections of the kidney and the liver were prepared from a tissue fixed in 4% paraformaldehyde and were observed with a confocal fluorescence microscope.

2. Results

Figure 18:
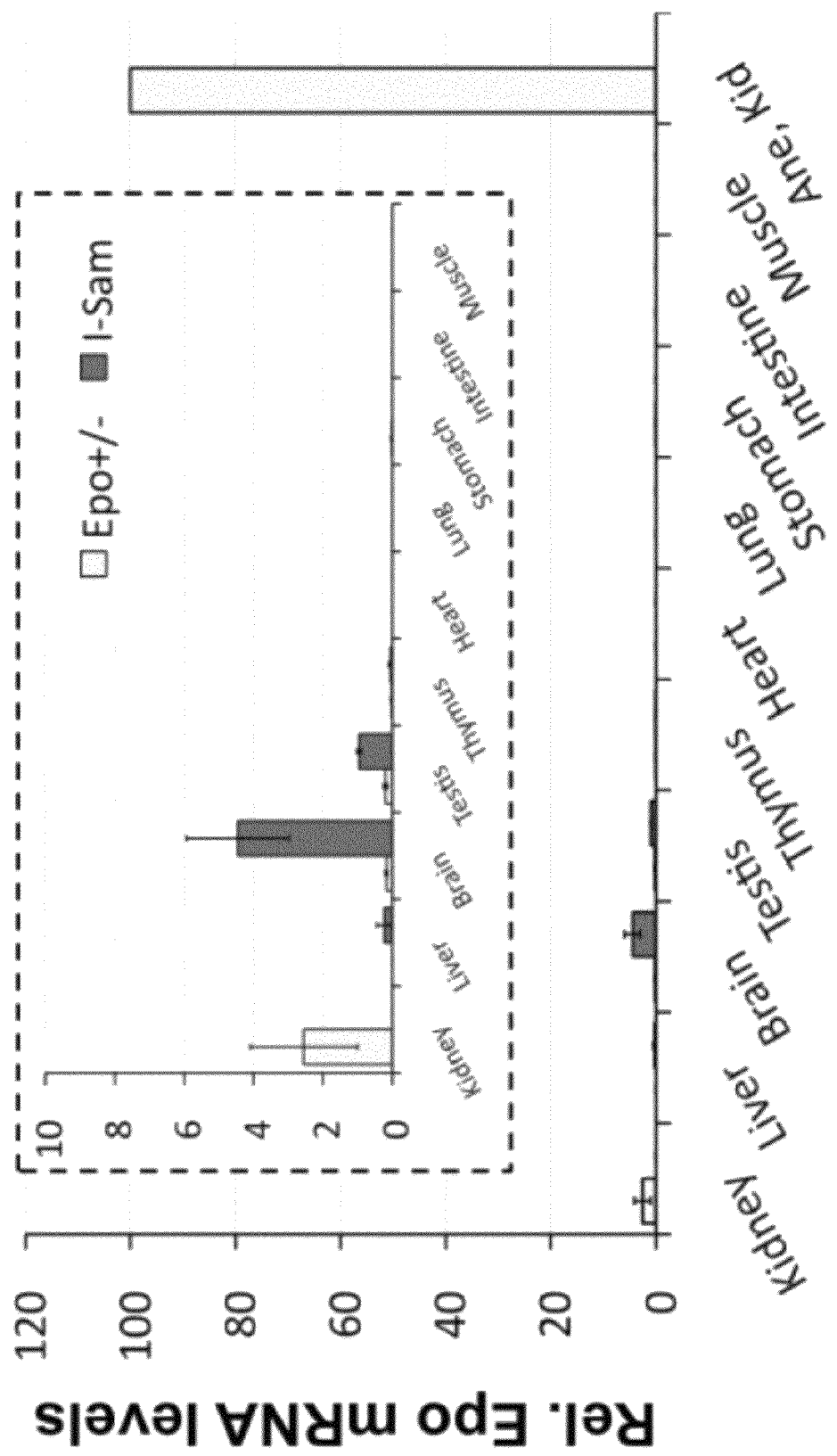
FIG. 18 is a graph showing Epo expression in the whole body of I-Sam, where the bars indicate, from the left, kidney, liver, brain, testis, thymus, heart, lung, stomach, intestine, muscle, and kidney in anemia (Ane, Kid: defined to be 100).
Figure 19:
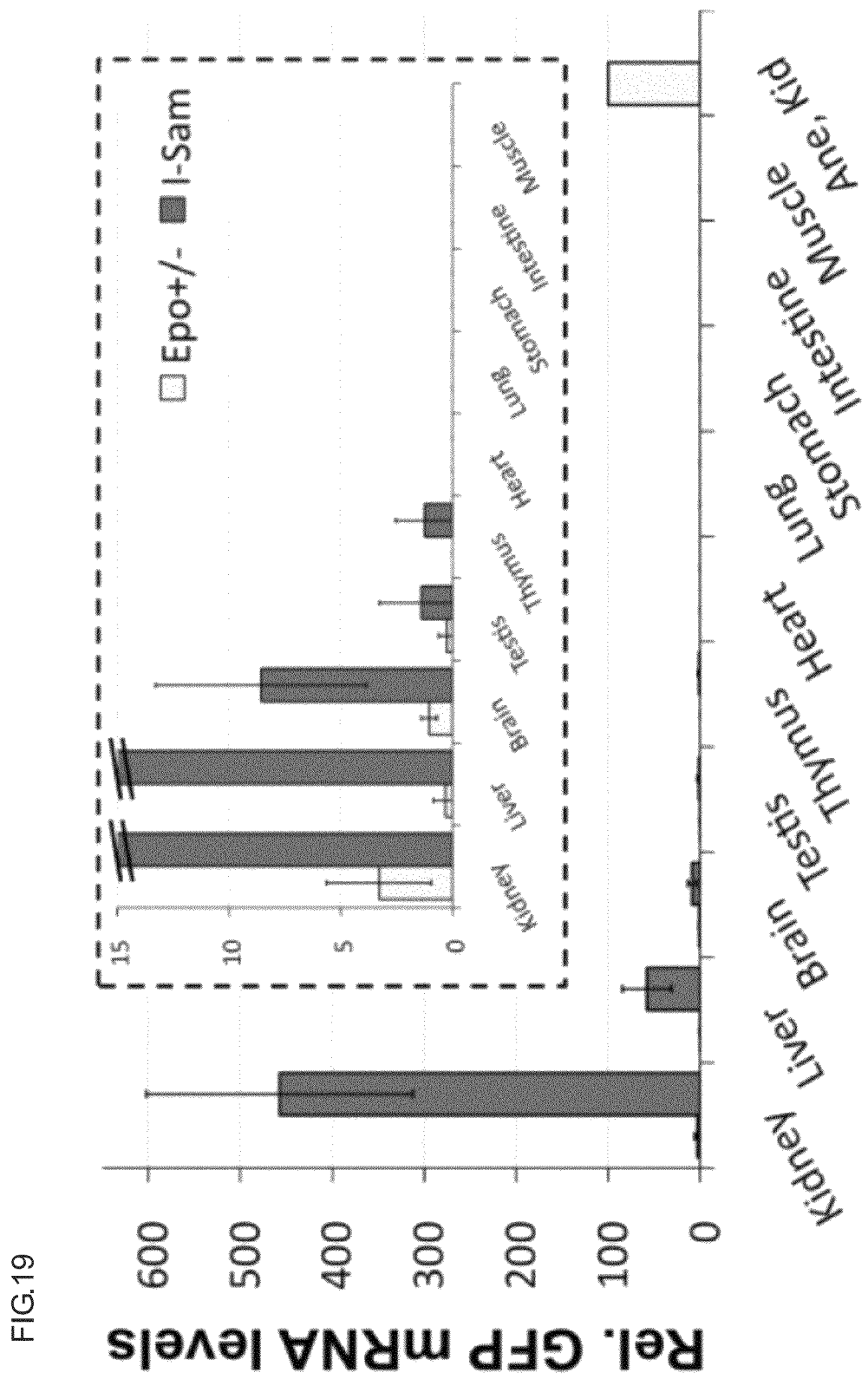
FIG. 19 is a graph showing GFP expression in the whole body of I-Sam, where the bars indicate, from the left, kidney, liver, brain, testis, thymus, heart, lung, stomach, intestine, muscle, and kidney in anemia (Ane, Kid: defined to be 100).

Analysis of Epo mRNA by quantitative RT-PCR did not recognize Epo mRNA expression in the kidney and the liver of I-Sam in spite of severe anemia. In the brain and the testis, Epo mRNA expression was recognized (FIG. 18). On the other hand, high GFP mRNA expression was recognized in the kidney and the liver of I-Sam, and the expression was also recognized in the brain (FIG. 19). It was confirmed that expression of the GFP gene introduced into the Epo gene locus is highly induced due to chronic anemia developed in I-Sam.

Figure 20:
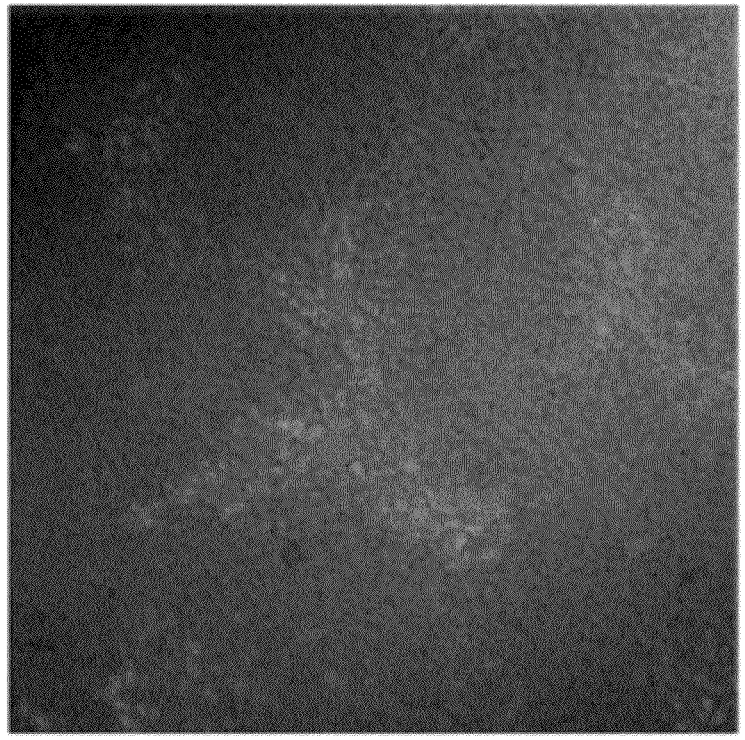
FIG. 20 includes photographs showing GFP-expressing cells in the kidney and the liver of I-Sam, where frozen sections prepared from a tissue fixed in 4% paraformaldehyde were observed with a confocal fluorescence microscope (left: kidney, right: liver).
Figure 20:
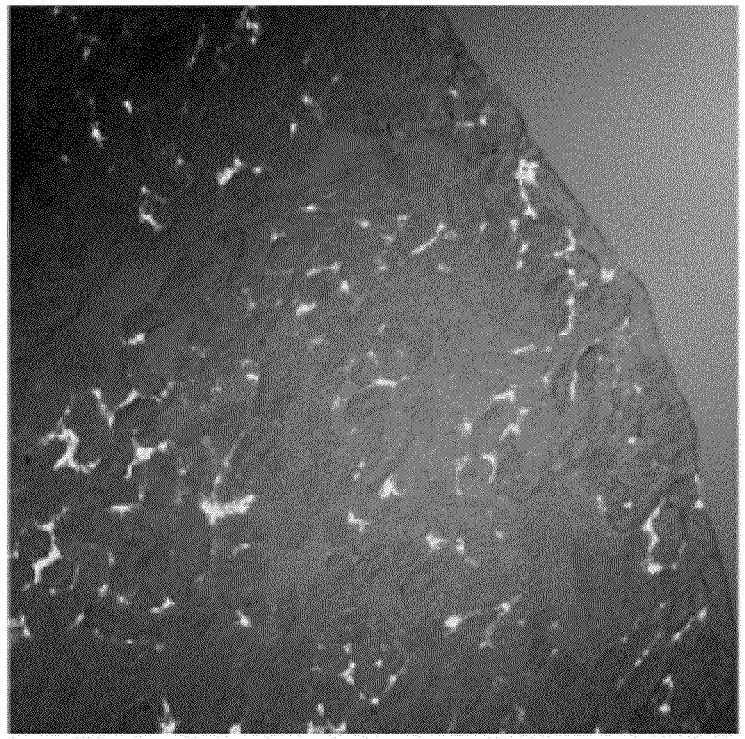

High expression of GFP was recognized by observation of the GFP fluorescence in the kidney and the liver of 1-Sam (FIG. 20). In the kidney, in general, Epo-producing cells are recognized exclusively within the stromal cells in the periphery of renal tubule of the cortex and medulla boundary (Obara, 2008). In I-Sam, the expression was limited within tubulointerstitial cells, but was recognized from the cortex surface to the depth of the medulla, and it was revealed that the cells having Epo-producing ability are increased by the lasting severe anemia and that the distribution of the cells varies. In addition, it was confirmed that the GFP-expressing cells increases in the periphery of the central vein in the liver.

Example 3

I-Sam expresses the GFP gene in the Epo-producing cells due to the chronic anemia, without stimulation such as blood removal. The expression of the Epo gene can be easily confirmed by the expression of the GFP gene not only in the tissue showing high expression of the Epo gene, such as the kidney and the liver, but also in the tissue showing low Epo expression. As an example, the expression of the Epo gene in the brain tissue was analyzed.

Figure 21:
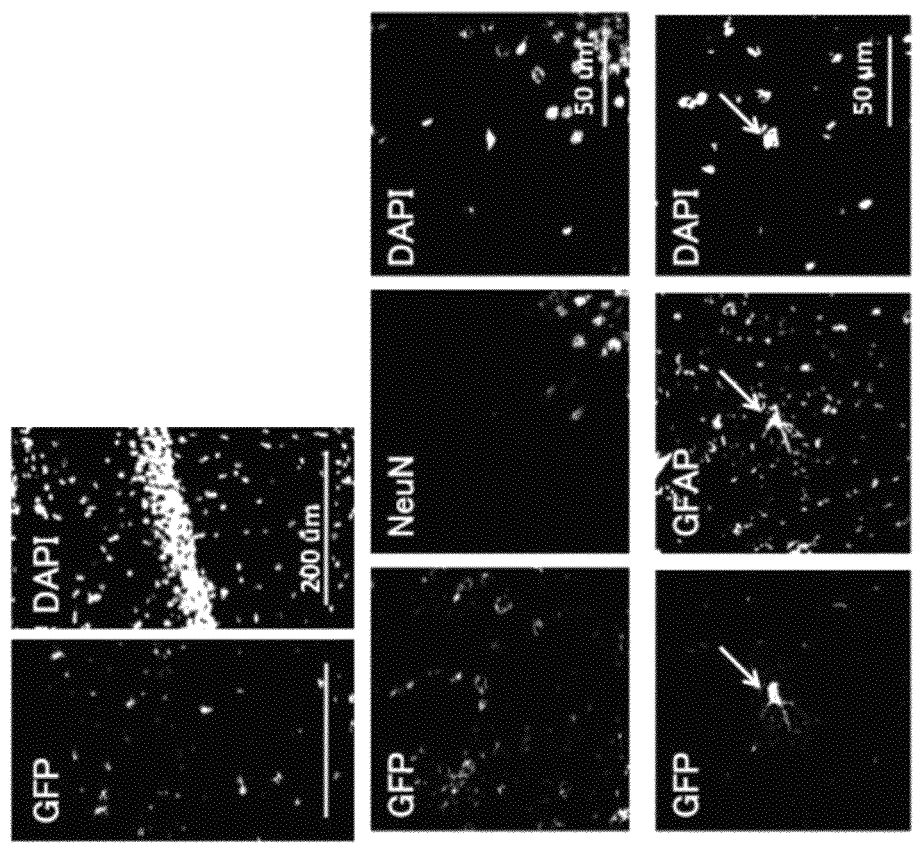
FIG. 21 includes photographs showing multiple immunofluorescence staining of the cerebrum of I-Sam, where GFP: image stained with an anti-GFP antibody, DAPI: nucleus image stained with DAPI, NeuN: nucleus image stained with an anti-NeuN antibody, GFAP: image stained with an anti-GFAP antibody, and arrow: cells expressing both GFP and GFAP.

As shown in Example 2 and FIG. 19, since the expression of the GFP gene was recognized in the brain, the basal ganglia portion was analyzed by immunohistochemical staining (FIG. 21). Specifically, in order to confirm what the GFP-positive cells are like, the GFP-positive cells in the brain tissue of I-Sam were subjected to multiple staining with a nerve cell marker, NeuN (which stains the nuclei of nerve cells), or an astrocyte marker (astrocyte), GFAP (which stains the cytoplasm of astrocytes).

As shown in FIG. 21, the results of the multiple immunohistochemical staining revealed that a large number of GFP-positive cells are present in the cerebrum. The results of the multiple staining with NeuN and GFAP confirmed that there are cells expressing both GFP and GFAP and that many of the GFP-positive cells are not nerve cells, but glia cells. The results suggest a possibility that Epo produced by glia cells adjacent to nerve cells works in a paracrine mode without being mediated by the cerebrovascular barrier to achieve a large effect.

Accordingly, it is possible to evaluate or screen for a drug that stimulates the intracerebral Epo production using I-Sam by, for example, experiments on ischemia/reperfusion of the nervous system on the assumption of treatment of, for example, cerebral infarction. Systemic administration of Epo has a possibility of increasing hemoglobin and raising the consistency of blood to lead to recurrence of cerebral infraction, but the possibility is low in a drug that specifically stimulates intracerebral Epo production. Accordingly, I-Sam is useful for evaluation of a safe and effective novel therapeutic agent for cerebral infarction.

INDUSTRIAL APPLICABILITY

The mouse of the present invention allows research on Epo-producing ability inherent in a tissue, research on the path and material that stimulate or suppress the Epo-producing ability, and analysis of reaction against chronic tissue hypoxia, without receiving the influence of endogenous Epo. Furthermore, it is possible to evaluate or screen for a drug that stimulates intracerebral Epo production using the GFP expression as an index by, for example, experiments on ischemia/reperfusion of the nervous system on the assumption of treatment of, for example, cerebral infarction. Accordingly, the mouse of the present invention can be used for research on, for example, erythropoietin, regular hematopoiesis and stress hematopoiesis, and activity of Epo other than the hematopoiesis as well as for development of a method of treating diseases, such as renal anemia and chronic anemia, in which Epo is involved.

All publications, patents, and patent applications cited in this specification are herein incorporated by reference in their entirety.

Accession Number

FERM BP-11347

SEQUENCE LISTING FREE TEXT

SEQ ID NO: 1: primer (GFP-cs)
SEQ ID NO: 2: primer (Epo-RTR)
SEQ ID NO: 3: primer (Epo-5UTRs)
SEQ ID NO: 4: primer (Epo-s5)
SEQ ID NO: 5: primer (Epo-B6 as)

| | | |
|---|---|---|
| 0-1 | PCT/RO/134 (SAFE) Indications relating to deposited | |
| 0-1-1 | microorganism or other biological material was prepared by: | PCT-SAFE Version 3.51.049.225 MT/ FOP 20110401/0.20.5.09 |
| 0-2 | International application number | |
| 0-3 | Reference number | PCG-9034WO |
| 1 | The indications made below relate to the deposited microorganism or other biological material referred to in the description | |
| 1-1 | Paragraph | 0057, 0098 |
| 1-3 | Identification of Deposit | |
| 1-3-1 | Name of depositary institution | IPOD International Patent Organism Depositary, National Institute of Advanced Industrial Science and Technology (IPOD) |
| 1-3-2 | Address of depositary institution | Tsukuba Central 6, 1-1, Higashi 1-chome Tsukuba-shi, Ibaraki-ken, 305-8566 Japan |
| 1-3-3 | Date of deposit | Mar. 1, 2011 |
| 1-3-4 | Accession number | IPOD FERM BP-11347 |
| 1-4 | Additional indication | None |
| 1-5 | Designated states for which indications are made | All designated states |
| 1-6 | Separate furnishing of indications | None |
| | For receiving Office use only | |
| 0-4 | This sheet was received with the international application (Yes/No) | |
| 0-4-1 | Authorized officer | |

REFERENCE TO A "SEQUENCE LISTING," A TABLE, OR A COMPUTER PROGRAM LISTING APPENDIX SUBMITTED AS AN ASCII TEXT FILE

The material in the ASCII text file, named "PCG-9034US_Sequence_Listing", created Sep. 26, 2013, file size of 1,111 bytes, is hereby incorporated by reference.

The invention claimed is:

1. A transgenic mouse developing anemia after birth by genetic modification, wherein the genetic modification comprises:
   (a) a homozygous knockout of an endogenous erythropoietin (Epo) gene in the genome of the mouse; and
   (b) introduction of an extraneous Epo gene, in a chromosome of the mouse, as a transgene, the transgene being a region from 3.3-kb upstream to 4.5-kb downstream of a transcription start site of the Epo gene,
   wherein:
   the mouse is hemizygous or homozygous for the extraneous Epo gene;
   expression of the extraneous Epo gene rescues the mouse from lethality by a shortage of Epo or anemia associated therewith before birth;
   expression of the extraneous Epo gene in the kidney is suppressed after birth; and
   the mouse was generated from a fertilized egg deposited under accession number FERM BP-11347.

2. The transgenic mouse according to claim 1, wherein a blood Epo concentration decreases after birth.

3. The transgenic mouse according to claim 2, wherein the postnatal Epo production in the kidney is suppressed by the genetic modification.

* * * * *

UNITED STATES PATENT AND TRADEMARK OFFICE
CERTIFICATE OF CORRECTION

Page 1 of 1

PATENT NO. : 9,180,207 B2
APPLICATION NO. : 14/008703
DATED : November 10, 2015
INVENTOR(S) : Masayuki Yamamoto et al.

It is certified that error appears in the above-identified patent and that said Letters Patent is hereby corrected as shown below:

In The Specification

Column 6, line 54, in the brief description of drawings section, please delete "(+/-)" and insert -- (+/+) --

Column 6, line 60, in the brief description of drawings section, please delete "—=—" and insert -- —●— --

Column 7, line 17, in the brief description of drawings section, please delete "(-/-)" and insert -- (+/-) --

Signed and Sealed this
Twenty-second Day of March, 2016

Michelle K. Lee
*Director of the United States Patent and Trademark Office*